(12) United States Patent
Chao et al.

(10) Patent No.: US 12,109,370 B2
(45) Date of Patent: *Oct. 8, 2024

(54) ARTERIAL CANNULA WHICH ALLOWS PROXIMAL AND DISTAL PERFUSION WITHIN A CANNULATED VESSEL

(71) Applicants: Tar Toong Victor Chao, Singapore (SG); Chong Hee Lim, Singapore (SG); Hock Heng Daniel Tan, Singapore (SG); Tze Kiat Ng, Singapore (SG)

(72) Inventors: Tar Toong Victor Chao, Singapore (SG); Chong Hee Lim, Singapore (SG); Hock Heng Daniel Tan, Singapore (SG); Tze Kiat Ng, Singapore (SG)

(*) Notice: Subject to any disclaimer, the term of this patent is extended or adjusted under 35 U.S.C. 154(b) by 117 days.

This patent is subject to a terminal disclaimer.

(21) Appl. No.: 16/592,640

(22) Filed: Oct. 3, 2019

(65) Prior Publication Data

US 2020/0215301 A1    Jul. 9, 2020

Related U.S. Application Data

(63) Continuation of application No. 15/115,368, filed as application No. PCT/SG2015/050010 on Jan. 30, 2015, now abandoned.

(30) Foreign Application Priority Data

Jan. 30, 2014    (SG) ................... 2014008510

(51) Int. Cl.
*A61M 25/00*    (2006.01)
*A61M 1/36*    (2006.01)
(Continued)

(52) U.S. Cl.
CPC ........ *A61M 25/007* (2013.01); *A61M 1/3659* (2014.02); *A61M 25/04* (2013.01); *A61M 25/10* (2013.01); *A61M 2205/583* (2013.01)

(58) Field of Classification Search
CPC ...... A61M 2025/1072; A61M 25/1002; A61M 2025/1059; A61M 1/3653; A61M 1/3659;
(Continued)

(56) References Cited

U.S. PATENT DOCUMENTS 4,687,471 A * 8/1987 Twardowski ......... A61M 1/285
604/175
4,995,866 A * 2/1991 Amplatz ........... A61M 25/0606
604/510

(Continued)

*Primary Examiner* — James D Ponton
*Assistant Examiner* — Hong-Van N Trinh

(57) ABSTRACT

A cannula includes a first segment configured to reside entirely within a vessel. The first segment includes a proximal exit opening disposed nearer to the heart, and multiple fenestrations disposed distally away from the proximal exit opening near a cannulation site. The fenestrations in combination with the proximal exit opening enable simultaneous perfusion of blood into the cannulated vessel along proximal and distal directions. During a medical procedure, blood introduced into a vessel (e.g., the femoral artery) by way of the cannula can exit the cannula in a manner that provides concurrent blood flow in a first set of directions proximally towards the heart and a second set of directions distally away from the heart. Radially displaceable anchoring elements positionable adjacent to the vessel's superficial wall aid retention of the first segment in the vessel. The fenestrations and/or anchoring elements can be arranged obliquely around portions of the cannula's circumference.

12 Claims, 19 Drawing Sheets

(51) Int. Cl.
*A61M 25/04* (2006.01)
*A61M 25/10* (2013.01)

(58) Field of Classification Search
CPC ........ A61M 1/3661; A61M 2025/0031; A61M 2025/0293; A61M 25/04; A61M 60/857; A61M 25/007; A61M 25/0075; A61M 25/0097; A61M 60/148; A61M 2025/1095; A61M 25/0029; A61M 25/0043; A61M 25/0052; A61M 25/0054; A61M 25/10; A61M 2205/583
See application file for complete search history.

(56) References Cited

U.S. PATENT DOCUMENTS

| | | | | |
|---|---|---|---|---|
| 5,697,946 | A * | 12/1997 | Hopper | A61B 17/3421 |
| | | | | 606/185 |
| 2014/0018619 | A1* | 1/2014 | Khoury | A61M 27/002 |
| | | | | 600/104 |
| 2015/0018725 | A1* | 1/2015 | Sommer | A61M 25/04 |
| | | | | 601/2 |

\* cited by examiner

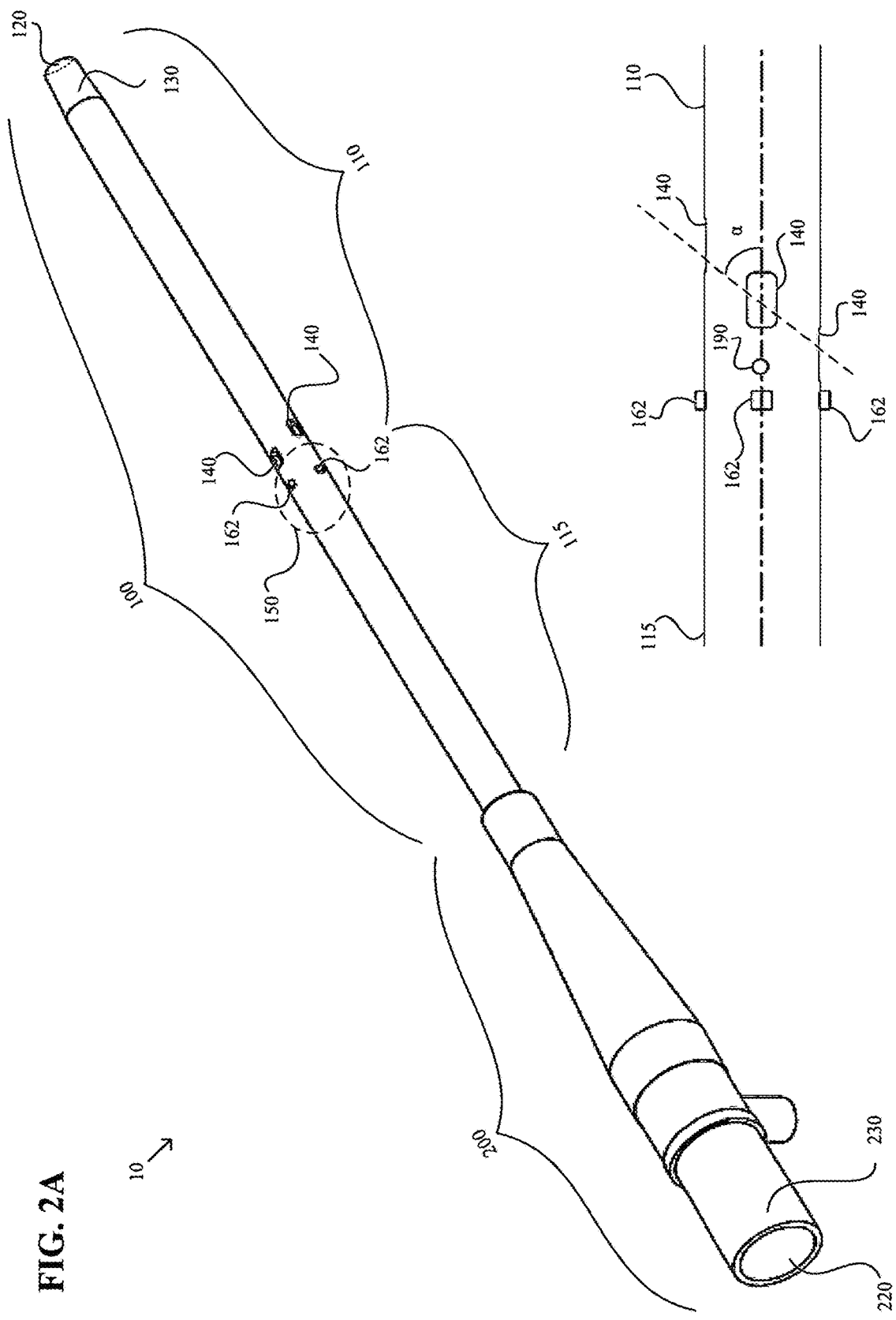

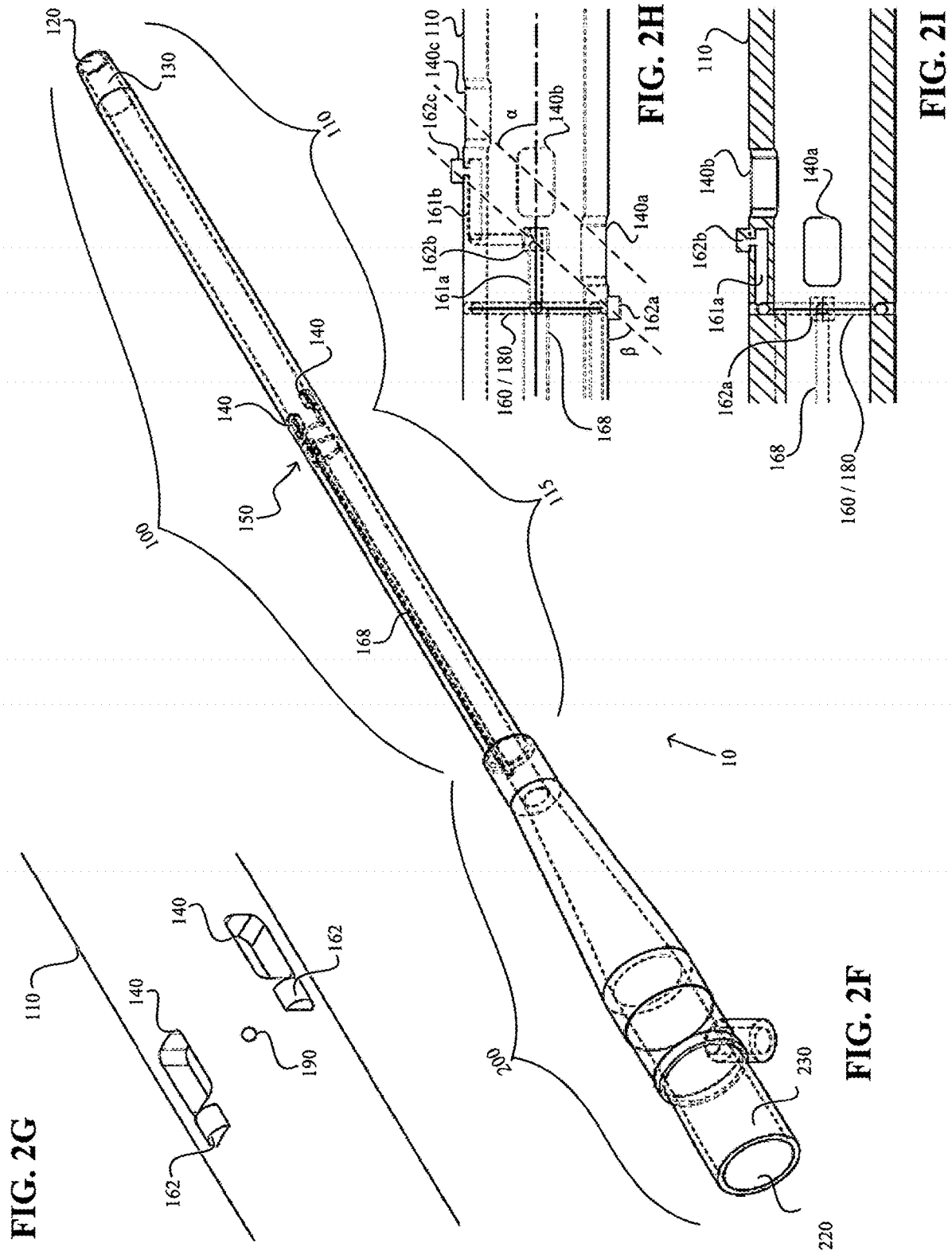

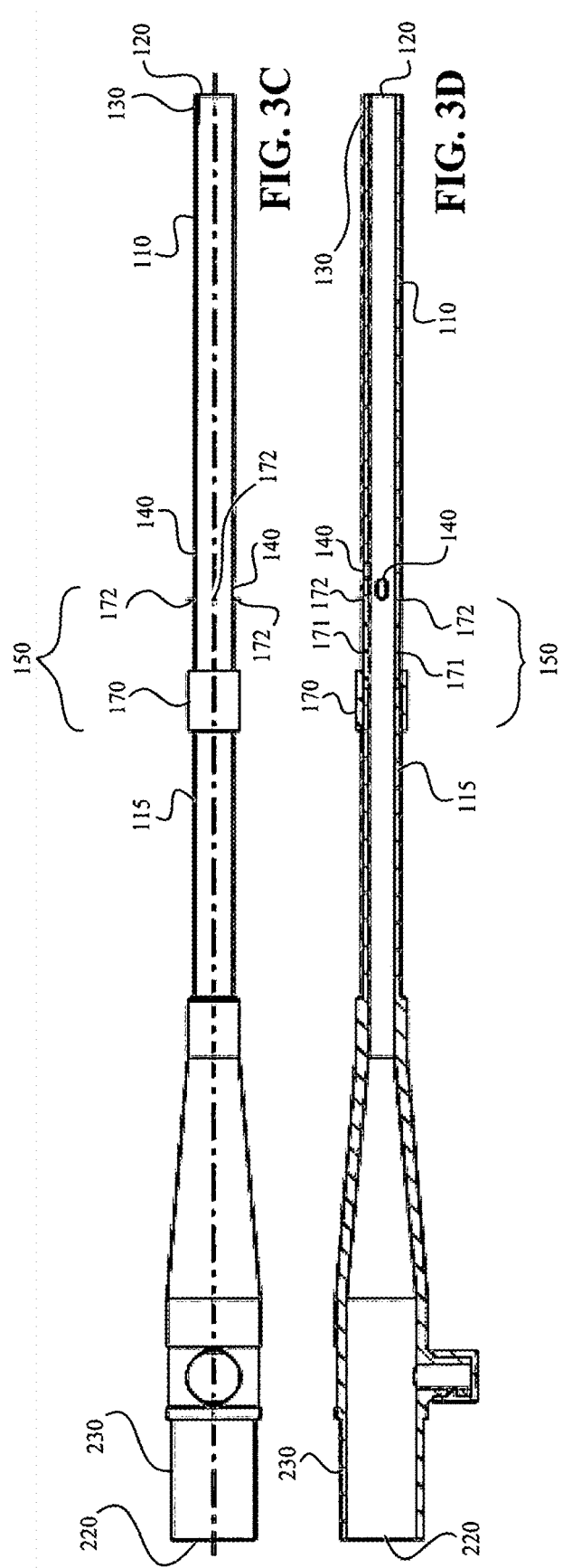

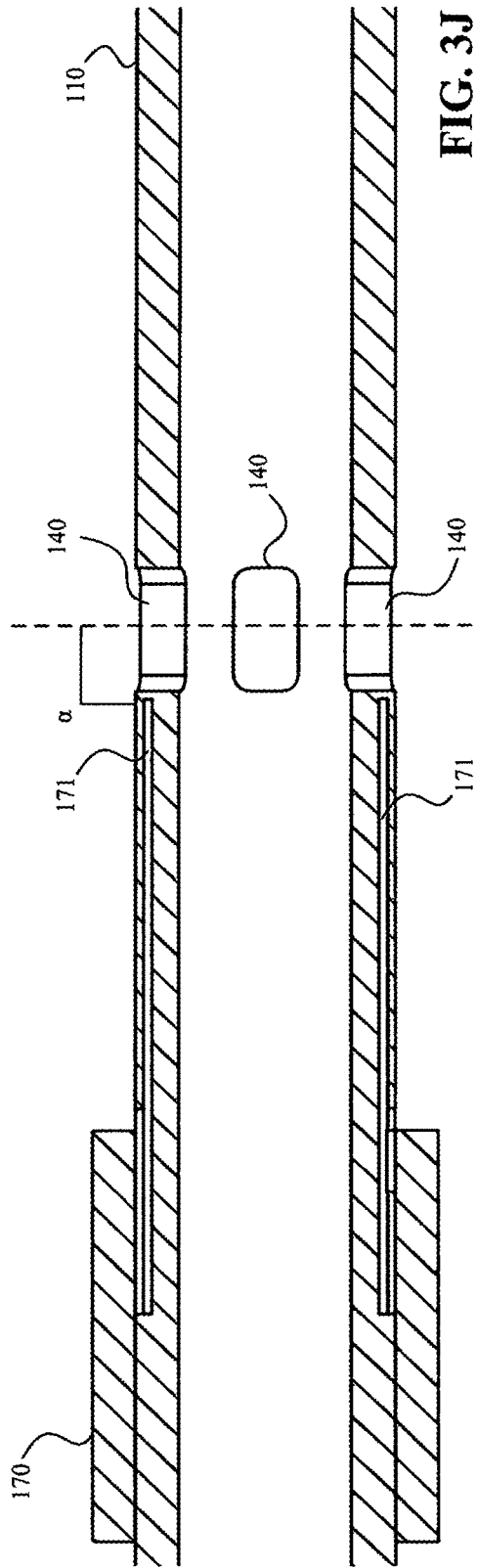
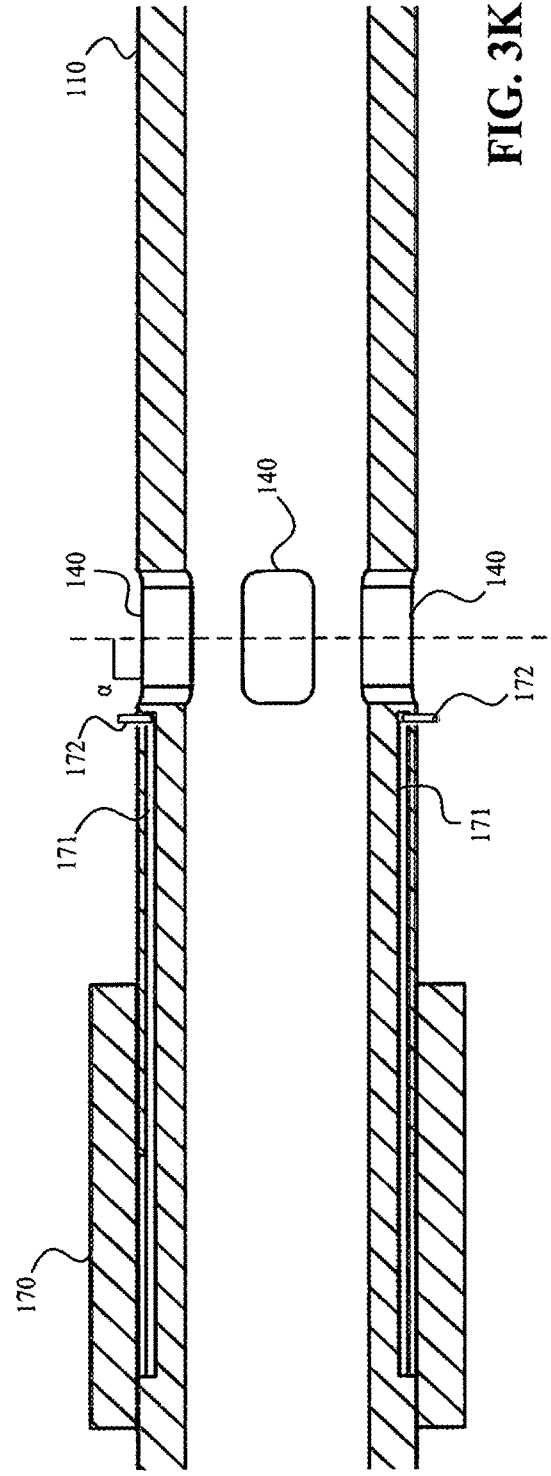

ARTERIAL CANNULA WHICH ALLOWS PROXIMAL AND DISTAL PERFUSION WITHIN A CANNULATED VESSEL

CROSS REFERENCE TO RELATED APPLICATIONS

This application is a continuation application claiming the benefit of priority from U.S. patent application Ser. No. 15/115,368, which was filed on 29 Jul. 2016, and which is incorporated herein by reference in its entirety.

TECHNICAL FIELD

Defining proximal as toward the heart and distal as away from the heart, aspects of the present disclosure are directed to a cannula configured for enabling fluid (e.g., blood) flow in both proximal and distal directions within a vessel by way of an extravascular distal end opening for receiving a fluid, an intravascular proximal end opening for outputting fluid in a proximal direction towards the heart, and multiple intravascular fenestrations disposed (e.g., obliquely) about portions of the cannula's periphery and length for enabling distal fluid flow away from the heart (e.g., down the limb in which the cannula is placed). A set of selectively activatable/expandable intravascular anchoring elements disposed (e.g., obliquely) distal to the fenestrations aid precise positioning of the fenestrations and secure retention of the cannula in the vessel.

BACKGROUND

Patients with cardiopulmonary failure can be treated with mechanical circulatory support, such as extra-corporeal membrane oxygenation (ECMO). In association with ECMO, a cannula having a distal end and a proximal tip placed in an artery, which is commonly the femoral artery, to infuse oxygenated blood into the body. The cannula can be inserted into the artery by way of open surgical or percutaneous puncture, such as through the Seldinger technique. Blood that is directed into the cannula's distal end exits the cannula at its proximal tip, and is directed up the aorta towards the heart. Another context in which a cannula such as this is used is cardiopulmonary bypass for heart surgery, including minimally invasive cardiac surgery, where cannulation is performed in a peripheral artery instead of the aorta (where cannulation is performed for majority of heart operations).

In order to supply an adequate amount of blood, the cannula needs to be sufficiently large in diameter. As a result, the cannula itself obstructs blood flow into the extremities and limbs that is cannulated, which is commonly a leg, though at times the axillary/subclavian artery, or even the neck vessel (especially in children/neonates) are accessed in certain clinical scenarios. For patients on long-term support, the potential for ischemia to the cannulated limb arises due to this obstruction of blood flow. There are a number of existing devices that provide for an introduction of catheters or cannulas into the artery or vessel.

U.S. Pat. No. 6,592,547 describes a device used for placement inside the patient's heart or aorta. However, a ring (46) is used to limit insertion of the cannula into the vessel. There is a need to introduce an additional step of suturing around the ring. In addition, the cannula (28) is positioned in the ascending aorta. The placement into the aorta might potentially lead to rupture or undesirable effects. While the device needs to be curved or angled at a distal portion so that fluid may be directed with or against natural flow, the natural flow occurrence suggests that the fluid flows only through the distal end.

U.S. Pat. No. 6,179,813 discloses a vascular access device for infusing fluid into a patient. There are a number of holes along the side of the vascular access device so that the fluid may exit the side holes. There is no concerted fluid flow for perfusing the vessel, nor is there an anchoring element in close relation to the holes, which are not concentrated to be along the path of blood flow, instead being positioned along the entire length of the cannula. In addition, the vascular access device is elongated without the need to be bendable, flexible, or capable of being bent. The incapability of bending will inadvertently create rupture to the artery when the vascular access device is twisted.

U.S. Pat. No. 5,178,611 describes yet another device as shown in FIG. 4 where there are at least two communication paths adapted to channel fluid outwardly. A first fluid communication path directs flow through at least one fenestration along a portion of the device. A second fluid communication path channels fluid towards a distal end of the device. Thus, there is a need to have at least two fluid communication paths to channel flow within the body. This would also mean a need to have a two-step approach for fluid communication. There is also no anchoring system in relation to the fenestrations.

U.S. Pat. No. 5,542,936 describes a device having anchor flaps, fenestrations, and a way to deploy the anchor flaps. FIGS. 9a and 9b describe an anchor flap used for anchoring the inner wall surface of the vessel. The anchoring of the device may potentially distort the internal profile of the superficial vessel wall, which is highly undesirable. The device has a line of fenestrations on one aspect of the circumference to allow distal perfusion, arranged along the length of cannula (longitudinally). While FIG. 8 seems to suggest that the flow will be disrupted heavily due to the concentration of the flow towards the wall of the vessel especially from fenestrations more proximal to the entry site (i.e., closer to the heart) and not in line with the line of the vessel lumen; there would be turbulent flow which may result in hemolysis (disruption of walls of red blood cells), also creating minimal amount of flow towards the opposite direction. Because the fenestrations are not circumferential, but only limited to one part of the circumference of the cannula, should the device be inserted in an oblique manner, i.e., not in line or parallel with the course of the vessel, which may occur in certain clinical situations, or be twisted, the fenestrations would direct flow toward the side wall of the vessel, resulting in turbulence, hemolysis and reduced flow.

U.S. Pat. No. 8,585,679 discloses an apparatus having multiple stages whereby a second stage provides a plurality of fenestrations where blood is directed inwardly axially along the internal portion of a tube. There is an additional suction required such that blood may be siphoned away from the heart. The apparatus is purely meant for use at the heart and not along the veins or artery.

U.S. Pat. No. 5,176,697 discloses a laparoscopic cannula for operating in the abdomen through small incisions. FIGS. 1 and 2 disclose the laparoscopic cannula when in use inserted through the body tissue. Thereafter, an inflatable balloon is inflated so that the laparoscopic cannula is fixed within the internal surface of the body tissue. The laparoscopic cannula is fixated in a substantially perpendicular manner.

U.S. Pat. No. 6,099,506 discloses different types of closure seals engaged at an incision to secure the cannula and prevent leakage of blood from the incision. FIGS. 1 to 8 show that the sealing effect must engage both a superficial vessel wall and a wall before entry into the superficial vessel wall.

U.S. Pat. No. 8,840,636 describes a mesh for filtering blood flow within a blood vessel. When the mesh is actuated, embolic materials entrap at the mesh. However, due to the need to inflate the mesh, the anchoring of the device creates an additional point of contact within the artery at the circumferential joint (317) and the entry point of the device. The additional point of contact within the artery potentially creates unwanted rupture within the artery. In addition, the cannula optionally contains openings in its distal end to further diffuse the cannula blood.

United States Patent Publication 2008/0294102 discloses a device having a balloon to inflate within the superior vena cava and inferior vena cava. The lateral openings that can presumably be fenestrations are positioned close to the opening which does not take into account of bi-directional flow as seen in FIG. 10. In addition, upon inflation of the balloon, the balloon cannulas seem to show that blood is only perfused in one direction and not bi-directionally.

U.S. Pat. No. 6,958,076 describes a venous valve primarily used for fluid flow in a first direction along a defined passageway while a second closed positon prevents fluid flow in a backward direction opposite of the first direction. The venous valve is primarily used for allowing one way flow of air into the inflatable cuff. The venous valve is used as a way to allow fluid to flow in only one direction.

U.S. Pat. No. 5,330,433 describes an arterial cannula which includes a diverting side hole which simultaneously perfuses blood to the body and the lower extremity. Two barbs on the cannula exterior position the diverting hole just inside the blood vessel and prevent the back wall of the blood vessel from blocking the diverting hole. However, because these barbs form a fixed protrusion from the otherwise smooth profile of the cannula, insertion of the cannula into the artery—may cause the artery wall to stretch and expand, thereby causing bleeding from around the cannula after insertion, especially if the blood pressure is at a higher level (practitioners in the art will know that bleeding from around the cannula may occur even in patients who are treated with existing standard arterial cannulae having smooth profiles). Because the diverting hole is single thus being limited to one part of the circumference of the cannula, should the device be inserted in an oblique manner, not in line or parallel with the course of the vessel, which may occur in certain clinical situations, or be twisted, the diverting side hole could direct flow toward the side wall of the vessel, resulting in turbulence, hemolysis and reduced flow. The fixed protrusion of the barbs would mandate open surgical removal of the cannula once its purpose is achieved, whereas the defect in a vessel in which a smooth cannula has been placed, after removal of said cannula, may be closed with percutaneous vessel closure devices/techniques currently available in the market.

U.S. Pat. No. 8,795,253 describes a bi-directional perfusion cannula that includes an elongate tube for insertion into an artery. The elongate tube has a first aperture at an end of the tube, an elbow formed in the elongate tube, and a second aperture formed in or slightly rearward of the elbow. The second aperture is the only aperture for distal blood flow, thus the second aperture must be sufficiently large. However, because the elbow forms a fixed protrusion from the otherwise smooth profile of the cannula, insertion of the cannula into the artery may cause the artery wall to stretch and expand, thereby causing bleeding from around the cannula after insertion, especially if the blood pressure is at a higher level (practitioners in the art will know that bleeding from around the cannula may occur even in patients who are treated with standard arterial cannulas with smooth profiles). Because the second aperture is only limited to one part of the circumference of the cannula, should the device be inserted in an oblique manner, i.e., not in line or parallel with the course of the vessel, which may occur in certain clinical situations, or be twisted, the second aperture would direct flow toward the side wall of the vessel, resulting in turbulence, hemolysis and reduced flow. The fixed protrusion of the elbow would mandate open surgical removal of the cannula once its purchase is achieved, whereas the defect in a vessel in which a smooth cannula has been placed, after removal of said cannula, may be closed with percutaneous vessel closure devices/techniques currently available in the market.

PCT publication WO 2014/021786 describes a cannula with multiple fenestrations that are maintainable in position substantially immediately or slightly beyond a site or point of cannula entry into a vessel. The fenestrations enable the simultaneous perfusion of blood into the cannulated vessel along multiple directions, including opposing or anti-parallel blood flow directions relative to a central axis of the cannulated vessel. However, the fenestrations are disposed transversely around the whole of the circumference of the cannula. The arrangement of the fenestrations may weaken the structural integrity of the cannula.

Although some existing devices and cannulas have been disclosed in the prior art, none of aforementioned devices and cannulas provides the benefits of the present disclosure. Therefore, a need exists for an arterial cannula that provides adequate blood flow into the body, but which also enables blood flow into the cannulated body extremity. The improved arterial cannula thus provides improvements in cannulation of the artery, thereby addressing at least some of the aforementioned problems.

SUMMARY

In accordance with an aspect of the present disclosure, a cannula structure is provided which is configured for cannulating a tubular anatomical vessel of a body of a patient, the tubular anatomical vessel having a superficial wall, wherein the cannula structure includes: (1) a first tube insertable into the tubular anatomical vessel through a cannulation point, the first tube having an elongate length and a lumen therethrough for infusing and channeling into the anatomical vessel a fluid, the first tube having: a distal fluid input configured for receiving the fluid; a first segment having a first lumen therethrough aligned with the lumen of the first tube and which is fluidically coupled to the distal fluid input, wherein the first segment has a lengthwise axis that extends through the first lumen, wherein the first segment is configured for residing entirely internal to the cannulated tubular anatomical vessel, and wherein a distal portion of the first segment includes a flexible or semi-flexible angulatable section; a second segment having a second lumen aligned with and integrally fluidically coupled to the first lumen, wherein the second segment is distal to the first segment and the flexible or semi-flexible angulatable section, and wherein the first and second lumens form the lumen of the first tube; a plurality of fluid outputs coupled to the distal fluid input and configured for discharging the fluid into the tubular anatomical vessel, wherein the plurality of fluid outputs includes: an exit opening disposed near or at a proximal end of the first segment, the exit opening configured for outputting or discharging a first portion of the fluid into the tubular anatomical vessel along a proximal flow direction that is (a) toward the patient's heart, and (b) parallel to the lengthwise axis of the first segment; and a set of fenestrations carried by distal portions of the first segment along portions of a length of the first segment and about portions of a circumference of the first segment on the flexible or semi-flexible angulatable section of the first segment, the set of fenestrations configured for outputting or discharging a second portion of the fluid into the tubular anatomical vessel such that the second portion of the fluid flows along a distal flow direction that is (a) away from the patient's heart, (b) parallel to the lengthwise axis of the first segment, and (c) opposite to the proximal flow direction; and (2) an anchoring assembly proximal to the second segment of the first tube and carried by the first segment of the first tube near or adjacent and distal to the set of fenestrations, wherein the anchoring assembly is configured for engagement with the superficial wall of the cannulated tubular vessel adjacent or just internal to the cannulation point, wherein the anchoring assembly includes at least one outwardly or radially displaceable structure that is coupled to one of an inflation tube and a slidably displaceable switch, and which is outwardly or radially displaceable away from the first lumen beyond an exterior surface of the first segment in response to clinician application of a positive pressure that introduces air or liquid into the anchoring assembly through the inflation tube or clinician displacement of the slidably displaceable switch, and wherein the anchoring assembly has a distal portion disposed closest to the cannula structure's distal end at a first circumferential position about the first segment and a proximal portion disposed closest to the cannula structure's proximal end at a distinct second circumferential position about the first segment such that the distal portion of the anchoring structure is closer to the second segment of the first tube than the proximal portion of the anchoring structure and the anchoring assembly is arranged obliquely with respect to the lengthwise axis of the first segment prior to angulation of the flexible or semi-flexible angulatable section of the first segment.

In an embodiment, the anchoring assembly incudes or is an inflatable cuff that is disposed about the first segment, and the inflation tube is fluidically coupled to a one-way valve assembly and the inflatable cuff.

The inflatable cuff can partially reside within portions of a wall thickness of the first segment.

The cannula structure of claim can further include a flow indicator assembly having: a fluid indicator port carried by the second segment distal to the anchoring assembly; and a fluidic channel coupled to the fluid indicator port, the fluidic channel including a transparent or translucent material capable of providing a visual indication of a flow of fluid from the tubular anatomical vessel into the fluid indicator port.

The flow indicator assembly can further include a luminous portion disposed along the fluidic channel, the luminous portion carrying a substance capable of reacting with the fluid within the fluidic channel to thereby enhance the visual indication of the flow of fluid in the fluidic channel.

In an embodiment, the anchoring assembly includes a plurality of outwardly or radially displaceable structures disposed about portions of the circumference of the first segment, wherein the plurality of outwardly or radially displaceable structures includes a first outwardly or radially displaceable structure disposed closest to the cannula structure's distal end, and a second outwardly or radially displaceable structure distinct from the first outwardly or radially displaceable structure and disposed proximal to the first outwardly or radially displaceable structure.

In such an embodiment, the set of fenestrations includes a first fenestration and a second fenestration disposed at different distal locations relative to each other along the first segment and different circumferential locations relative to each other along the first segment, and wherein the first outwardly or radially displaceable structure is disposed distal to the first fenestration, and the second outwardly or radially displaceable structure is disposed distal to the second fenestration.

The anchoring assembly can include (a) an inflatable cuff, or (b) a rigid or generally rigid annular fluid transport channel fluidically coupled to the plurality of outwardly or radially displaceable structures.

In an embodiment, the anchoring assembly includes the inflatable cuff, wherein the plurality of outwardly or radially displaceable structures includes a plurality of flange members fluidically coupled to the inflatable cuff, and wherein each of the plurality of flange members is outwardly or radially displaceable away from the first lumen in response to inflation of the inflatable cuff.

Each of the plurality of flange members can be configured to protrude away from and beyond the exterior surface of the first segment responsive to inflation of the inflatable cuff while the inflatable cuff (i) resides at least partially within the thickness of a wall of the first segment, or (ii) remains internal to the exterior surface of the first segment.

In an embodiment, the anchoring assembly includes the slidably displaceable switch, wherein the slidably displaceable switch is coupled to a plurality of thin flexible strips of material that extend along and within a wall of the second segment of the first tube and which terminate distal to the set of fenestrations, wherein the at least one outwardly or radially displaceable structure includes a plurality of petals, wherein each of the plurality of petals is coupled to or formed from an end portion of a corresponding strip of material, wherein responsive to activation of the slidably displaceable switch, each end portion is configured to extend outwardly beyond the exterior surface of the first segment at a different distal location along the first segment and a different circumferential location about the first segment, and wherein each different distal location is distal to the set of fenestrations.

The set of fenestrations can include a first fenestration and a distinct second fenestration, wherein the plurality of petals includes a first petal corresponding to the first fenestration, and a second petal corresponding to the second distinct fenestration.

The cannula structure can further include a second tube configured for mating engagement with the first tube and which serves as a dilator relative to the first tube.

BRIEF DESCRIPTION OF THE DRAWINGS

FIG. 3A-3M illustrate aspects of representative catheters that include anchoring assemblies having slidably displaceable elements in accordance with particular embodiments of the present disclosure.

DETAILED DESCRIPTION

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range or the use of terms such as approximately or about is understood to include or be a recitation of an approximate numerical value or value range (e.g., within +/-2%, +/-5%, +/-10%, or +/-20%).

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include, be, or be a portion of a system, an apparatus, a device, a structure, an object, a process, a physical parameter, or a value depending upon the type of set under consideration.

As used herein, proximal is defined as toward or closer to the heart; and distal is defined as further away from the heart or in a direction away from or opposite to proximal with respect to fluid flow. The term "vessel" is taken to mean an anatomical vessel, passage, or channel (e.g., a blood vessel, such as an artery) of a patient or subject, or an anatomical chamber or compartment. The term "perfusion" is taken to mean the injection, transfer, or communication of blood and/or one or more other fluids into a vessel for purpose of enabling the blood and/or other fluid(s) to reach an organ or tissues (e.g., to supply nutrients and oxygen thereto). The term "fluidically coupled" is taken to mean coupled in a manner that provides for fluid (e.g., liquid/gas) transfer or communication.

Figure 1A:
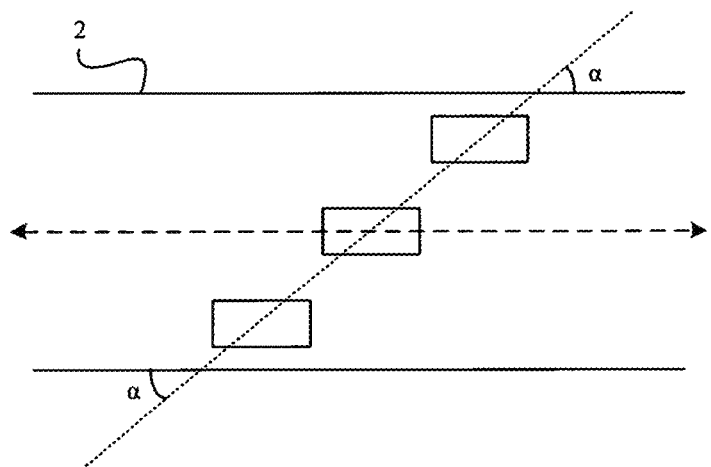
FIG. 1A and FIG. 1B are diagrams of representative oblique arrangements in accordance with the present disclosure.
Figure 1B:
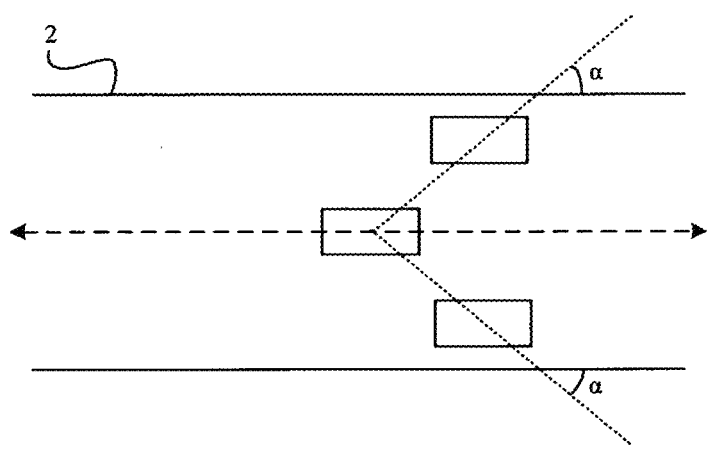

The term "oblique" or "obliquely" is taken to mean at an angle that is neither a right angle nor a multiple of a right angle relative to or along a lengthwise reference segment, section, or axis (e.g., a central longitudinal axis or a peripheral edge, border, or boundary) of a vessel or a tubular structure disposed therein, and/or a direction of fluid flow (e.g., proximal fluid flow) in the vessel or tubular structure. Representative examples of oblique arrangements or orientations of structures within a tubular structure or vessel 2 are shown in FIG. 1A-FIG. 1B. An angle that is oblique can be measured relative to a lengthwise axis or a fluid flow direction and a line or plane defined across or through the tubular structure or vessel 2, for instance, a line or plane corresponding to the positions of a plurality of structures carried by the tubular structure or vessel 2. An individual having ordinary skill in the art will readily understand that various oblique arrangements or orientations are possible in accordance with embodiments of the present disclosure.

Figure 1C:
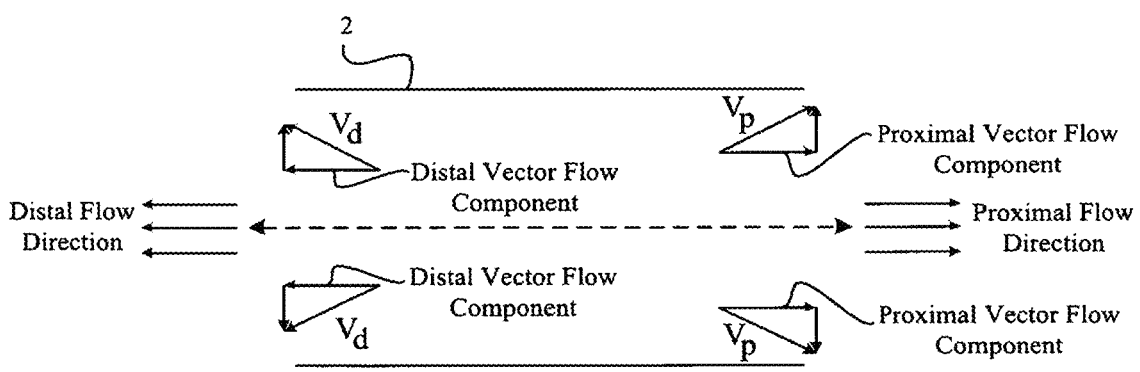
FIG. 1C illustrates representative proximal fluid flow(s), proximal vector fluid flow components, distal fluid flow(s), and distal vector fluid flow components in a tubular structure in accordance with an embodiment of the present disclosure.

The term "distal vector flow component" means a distally directed component of a fluid flow vector $V_d$ within a vessel 2 where distally directed is defined as a direction that is parallel to a lengthwise/longitudinal/central axis of the vessel 2 along which fluid flows, and opposite to a proximally directed fluid flow that is also parallel to the lengthwise/longitudinal/central axis of the vessel 2. Correspondingly, the term "proximal vector flow component" means a proximally directed component of a fluid flow vector $V_p$ within the vessel 2, where proximally directed is defined as a direction that is parallel to the lengthwise/longitudinal/central axis of the vessel 2, and opposite to a distally directed fluid flow. Representative proximal fluid flows, proximal fluid flow vectors $V_p$, proximal vector flow components, distal fluid flows, distal fluid flow vectors $V_d$, and distal fluid flow components with respect to a representative vessel 2 are illustrated in FIG. 1C.

Structural and Functional Overview

Embodiments in accordance with the present disclosure are directed to a cannula or cannula structure (e.g., an arterial cannula) providing (a) an exit opening at a proximal cannula portion, segment, end, or tip that is configured for entry into a vessel (e.g., an artery) at a cannulation site or point, and which is configured for displacement or travel along internal portions of the vessel and positioning away from the cannulation point; and (b) a set of fenestrations, apertures, windows, or openings configured to be positioned or maintained in position within the vessel essentially, substantially, or nearly immediately beyond the cannulation point. The cannula is configured to channel a flow or volume of blood and/or another fluid along a least resistive pathway through a lumen of the cannula with considerable laminar flow in a first direction proximally towards the heart when a portion of the lumen is positioned within the cannulated vessel. The set of fenestrations, in association with the exit opening at the cannula's proximal tip, enable simultaneous perfusion of blood and/or another fluid into the cannulated vessel along multiple fluid flow directions, including both proximal and distal fluid flow directions. More particularly, a first amount, portion, or volume of blood/fluid is discharged from the exit opening into the vessel in a first flow direction towards the heart, and a second amount, portion, or volume of the blood is discharged from the set of fenestrations into the vessel in a set of flow directions away from the heart. Thus, blood introduced into the vessel by the cannula simultaneously flows towards the heart, i.e. proximally, and away from the heart, i.e. distally.

FIG. 2A-FIG. 3M show schematic illustrations of portions of representative cannula assemblies, cannula structures, cannula devices, or cannulas (e.g., an arterial cannula) in accordance with particular embodiments of the present disclosure. As indicated such FIGs., the cannula includes at least a first tube, tubular member, or tubular structure 10 providing a lumen therethrough and having an elongate first portion 100 coupled to a second portion 200, where the second portion 200 is distal to the first portion 100. The first portion 100 spans, extends along, or defines an elongate first fraction of the length of the first tube 10; and the second portion 200 spans, extends along, or defines a second fraction of the first tube's length. The first and second portions 100, 200 of the first tube 10 are coupled, joined, or formed together (e.g., integrally formed together) to enable fluid flow from a distal opening 220 disposed at a distal end 230 of the first tube 10 toward, to, and through a proximal exit opening, proximal end opening, or proximal opening 120 disposed at, along, adjacent, or contiguous to a proximal portion, segment, end, or tip 130 of the first tube 10. In several embodiments, the proximal end portion/tip 130 is tapered to facilitate smooth insertion into a vessel. One having ordinary skill in the art will readily understand that the first tube 10 can itself be defined as the cannula, and hence the first tube's distal opening 220 can be identified or defined as the cannula's distal opening 220, and the first tube's proximal exit opening 120 can be defined as the cannula's proximal exit opening 120.

The first portion 100 of the first tube 10 includes a first or proximal segment 110 that spans or extends along a first section of the first tube's elongate length, and which has a first lumen therethrough which forms a portion of the first tube's lumen. The first segment 110 is coupled (e.g., integrally and fluidically coupled) to a second or distal segment 115 of the first portion 100, which spans or extends along a second section of the first tube's elongate length, and which has a second lumen therethrough (that is contiguous or aligned with the first lumen). The first segment 110 is configured for entering into a vessel (e.g., an artery) at a cannulation site or point, and being positioned or displaced along or within the vessel such that the proximal tip 130 of the first tube 10 resides at an intended or predetermined distance away from the cannulation point, at which blood and/or another fluid is intended to be perfused or directed into the cannulated vessel along a first or primary flow direction through the first tube's proximal exit opening 120. The first flow direction is the proximal direction going towards the heart.

The first segment 110 carries a set of fenestrations 140 and a cannula retention or anchoring assembly 150. The set of fenestrations 140 and the first tube's proximal exit opening 120 are configured for fluid communication with the first tube's distal opening 220 and the second portion 200 by way of the first tube's first and second segments 110, 115. Blood and/or another fluid supplied to the first tube's distal opening 220 flows towards the set of fenestrations 140 as well as the first tube's proximal exit opening 120. As further detailed below, the set of fenestrations 140 provide fluid output, discharge, or release sites, ports/portals, or points other than the first tube's proximal exit opening 120 by which blood and/or another fluid can enter into the cannulated vessel from the first segment 110 and flow in a set of directions away from, different than, or in opposition to a proximal blood/fluid flow direction out of and beyond the first tube's proximal exit opening 120 (or stated equivalently, the set of fenestrations 140 provides sites at which blood/fluid can exit the first segment 110, enter the cannulated vessel, and flow in a distal direction). Hence, the set of fenestrations 140 provides sites through which blood/fluid (e.g., oxygenated blood) that is supplied to the first tube's distal opening 220 can flow into and travel within the cannulated vessel along a second or secondary direction that is different from or opposite to the aforementioned first direction that is associated with the first tube's proximal exit opening 120. The cannula of the present disclosure thus advantageously eliminates the need for a second or separate cannula to direct blood flow in the distal direction, as the cannula of the present disclosure is able to enable or direct blood flow in both proximal and distal directions in a simultaneous manner.

The anchoring assembly 150 includes a set of anchoring elements configured for selective activation or deployment away from and beyond outer or exterior portions of the first tube's first segment 110, and subsequent abutment against or engagement with the cannulated vessel's superficial wall, adjacent or just internal to the cannulation point, to thereby facilitate reliable retention or anchoring of the first tube 10 within the cannulated vessel in a manner that facilitates or enables predictable/precise positioning of the cannula's proximal exit opening 120 and the fenestrations 140 within the cannulated vessel. Such anchoring elements are also configured for selective deactivation or retraction prior to withdrawal of the cannula from the cannulated vessel. Depending upon embodiment details, the anchoring elements can be coupled to or include outwardly or radially displaceable/expandable and inwardly or radially displaceable/retractable elements, such as fluid (e.g., gas or liquid) pressurizable or inflatable/depressurizable or deflatable elements, e.g., a balloon or cuff 160 and/or flange elements, structures, or members 162, as indicated in FIGS. 2A-2N and further described in detail below; or slidably, progressably incrementally, and/or stepwise displaceable structures that can laterally or radially extend away from the outer or exterior surface of the first tube's first segment 110, for instance, in the form of projections, protrusions, or stub-like structures, e.g., petals 172, as indicated in FIGS. 3A-3M and further described in detail below.

In some embodiments, a boundary or dividing line between the first segment 110 and the second segment 115 of the first tube's first portion 100 can be defined at a distal edge or border of the anchoring assembly 150 or the set of anchoring elements associated therewith (e.g., with respect to a distal-most edge or border of the fenestrations 140). Portions of the anchoring assembly 150 or the anchoring element(s) can be positioned at or approximately at or generally near the middle of the first tube 10, depending upon embodiment details. Depending upon embodiment details, the first segment 110 can span up to approximately 70%-80% of the length of the first portion 100. Typically, the second segment spans approximately 20%-50% of the length of the first portion 100.

In various embodiments, the cannula also carries a blood/fluid indicator assembly, which can include a blood/fluid indicator port 190 disposed on the first segment 110 or second segment 115 depending upon embodiment details, at a location near or very near to the fenestrations 140 and/or the anchoring assembly's anchoring elements When the cannula enters a vessel, blood/fluid within the vessel can enter and flow into the blood/fluid indicator port 190, and flow through portions of the blood/fluid indicator assembly to provide an indication (e.g., a visual indication) that the fenestrations 140 and the anchoring elements are located at or approximately at an intended location, and the cannula need not be advanced further into the vessel. Additional details of representative blood/fluid indicator assemblies are further described below.

The second portion 200 of the first tube 10 extends distally away from the second segment 115 of the first tube's first portion 100, toward and to the first tube's distal opening 220. A distal end 230 of the second portion 200 can provide or be a standard physical interface, coupling, or connection configured for mating engagement with and receiving blood and/or another fluid from a structure or device (e.g., a portion of an ECMO or cardiopulmonary bypass system) that is separate or separable from the first tube 10, in a manner readily understood by an individual having ordinary skill in the relevant art.

Figure 3A:
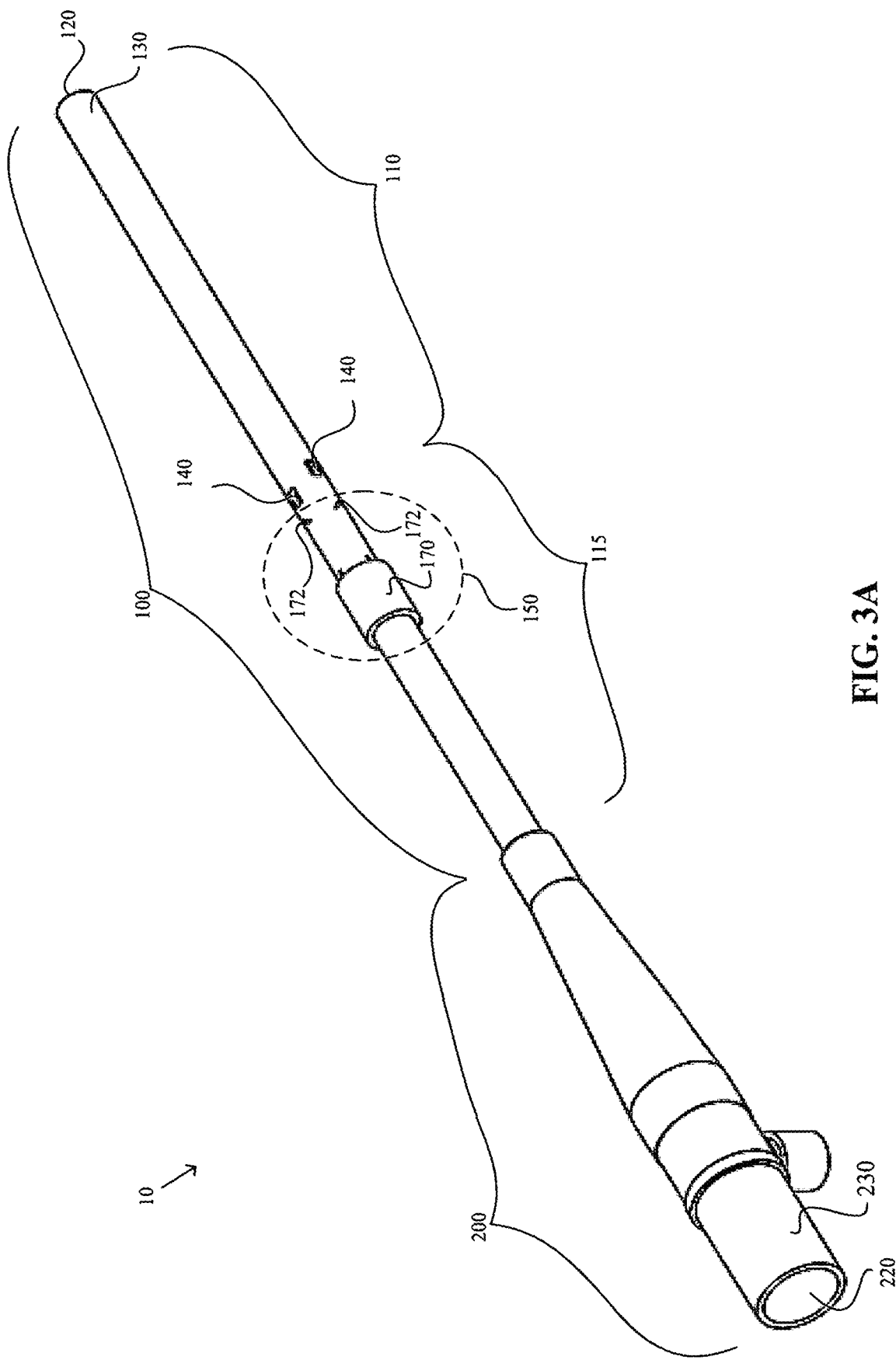
Figure 3B:
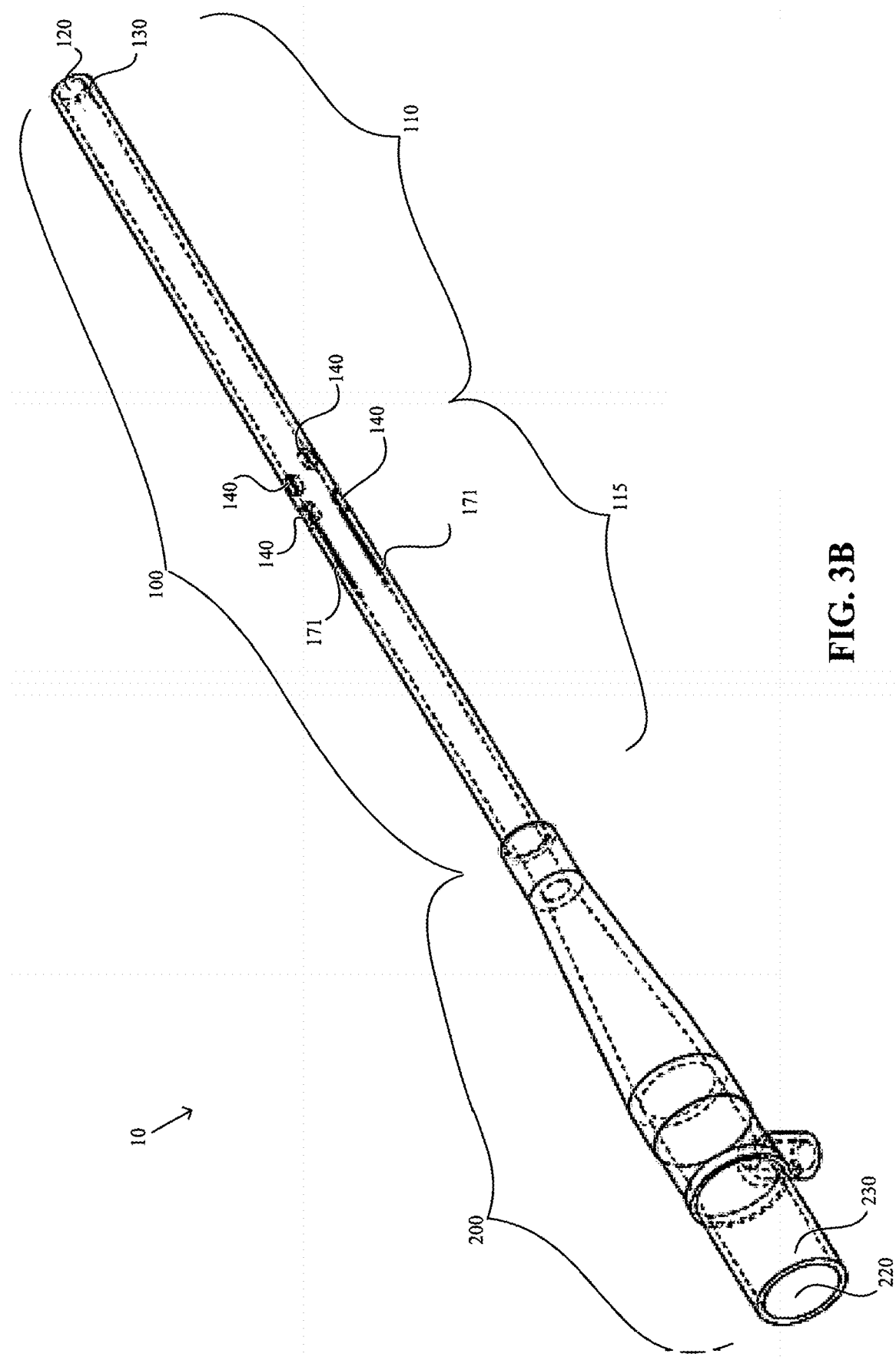
Figure 3F:
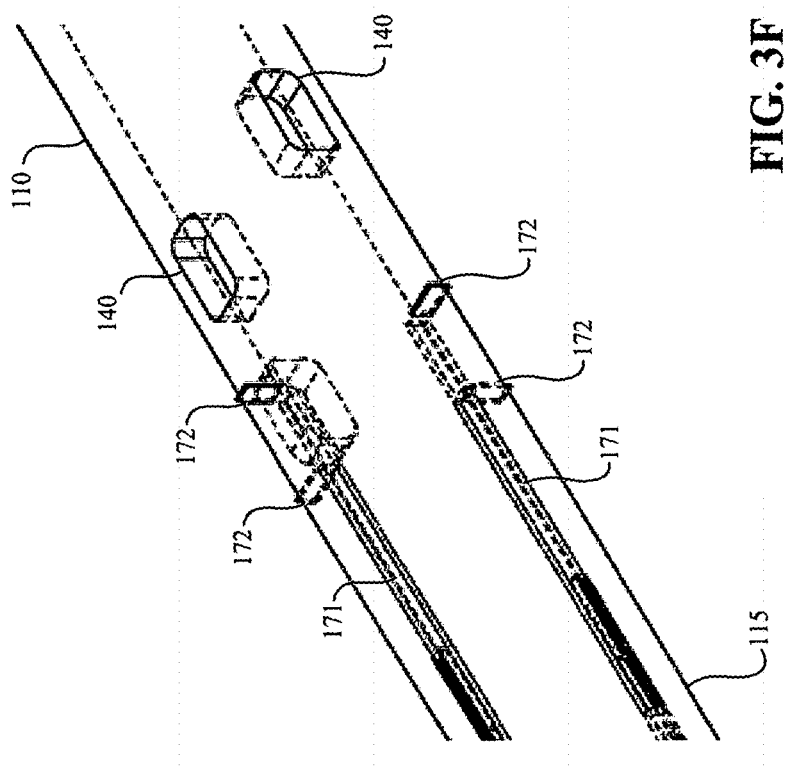
Figure 3E:
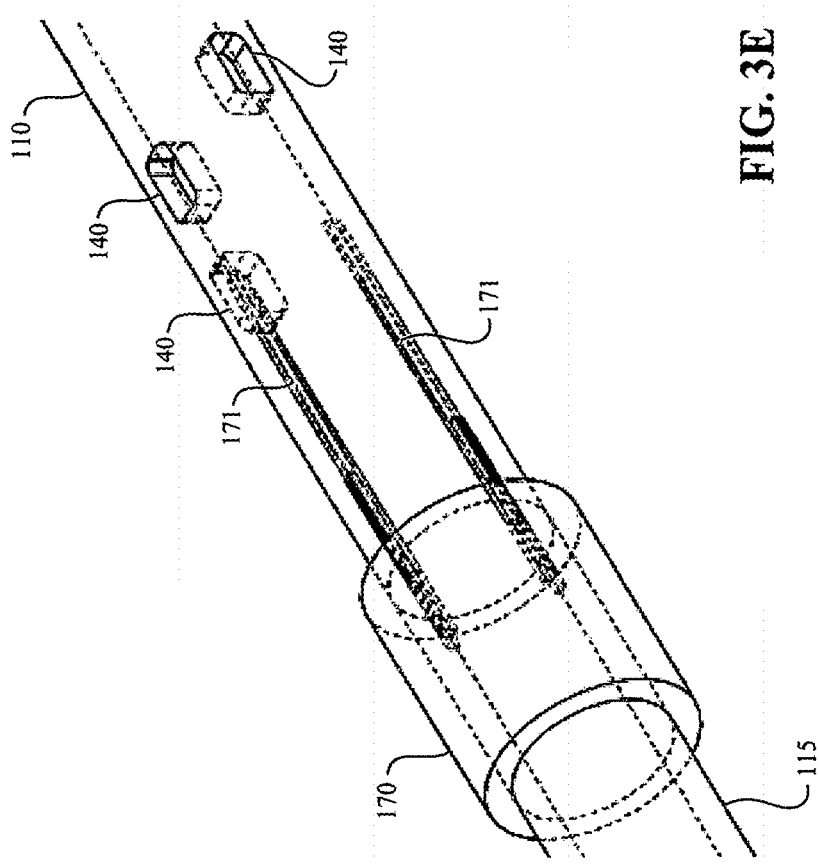
Figure 3G:
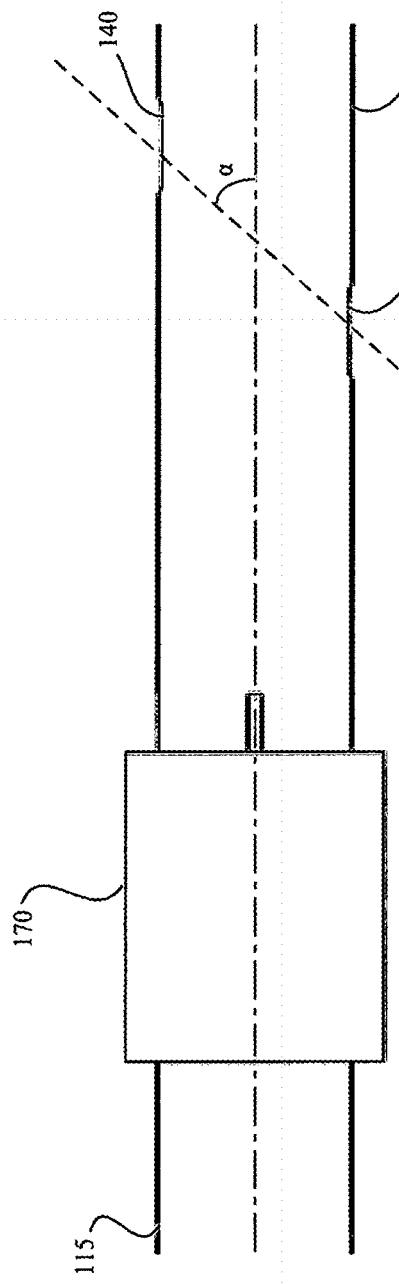
Figure 3H:
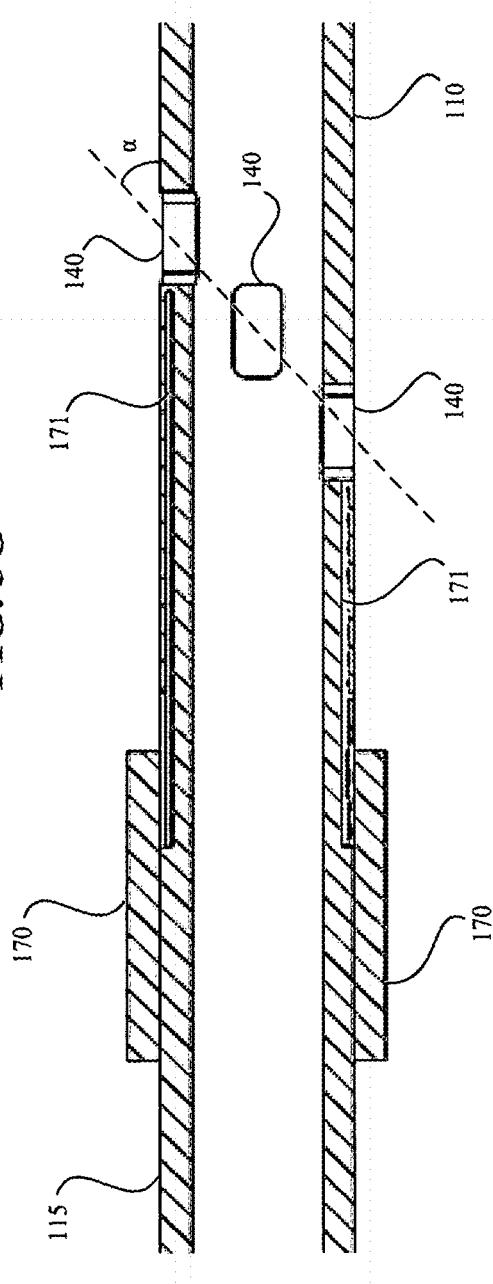
Figure 3I:
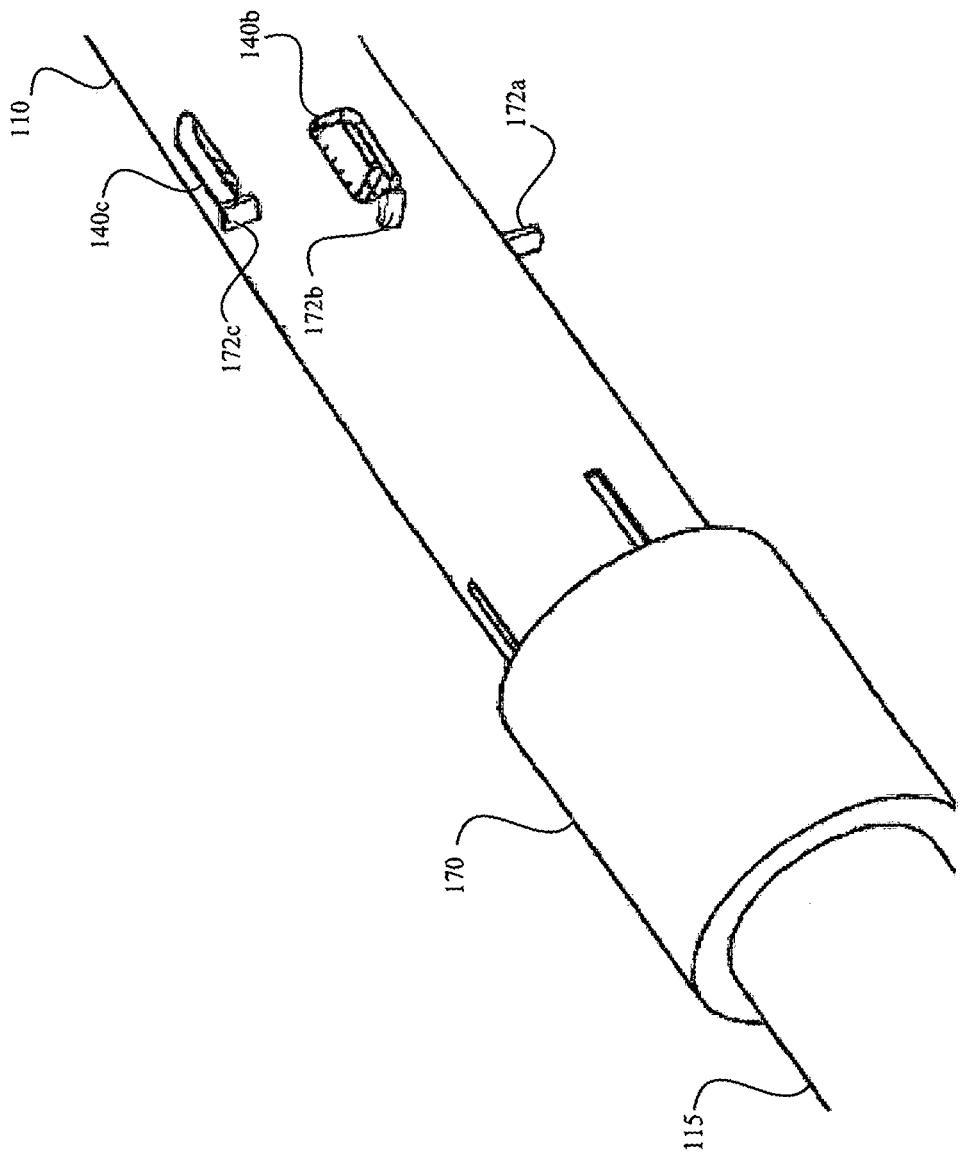
Figure 3L:
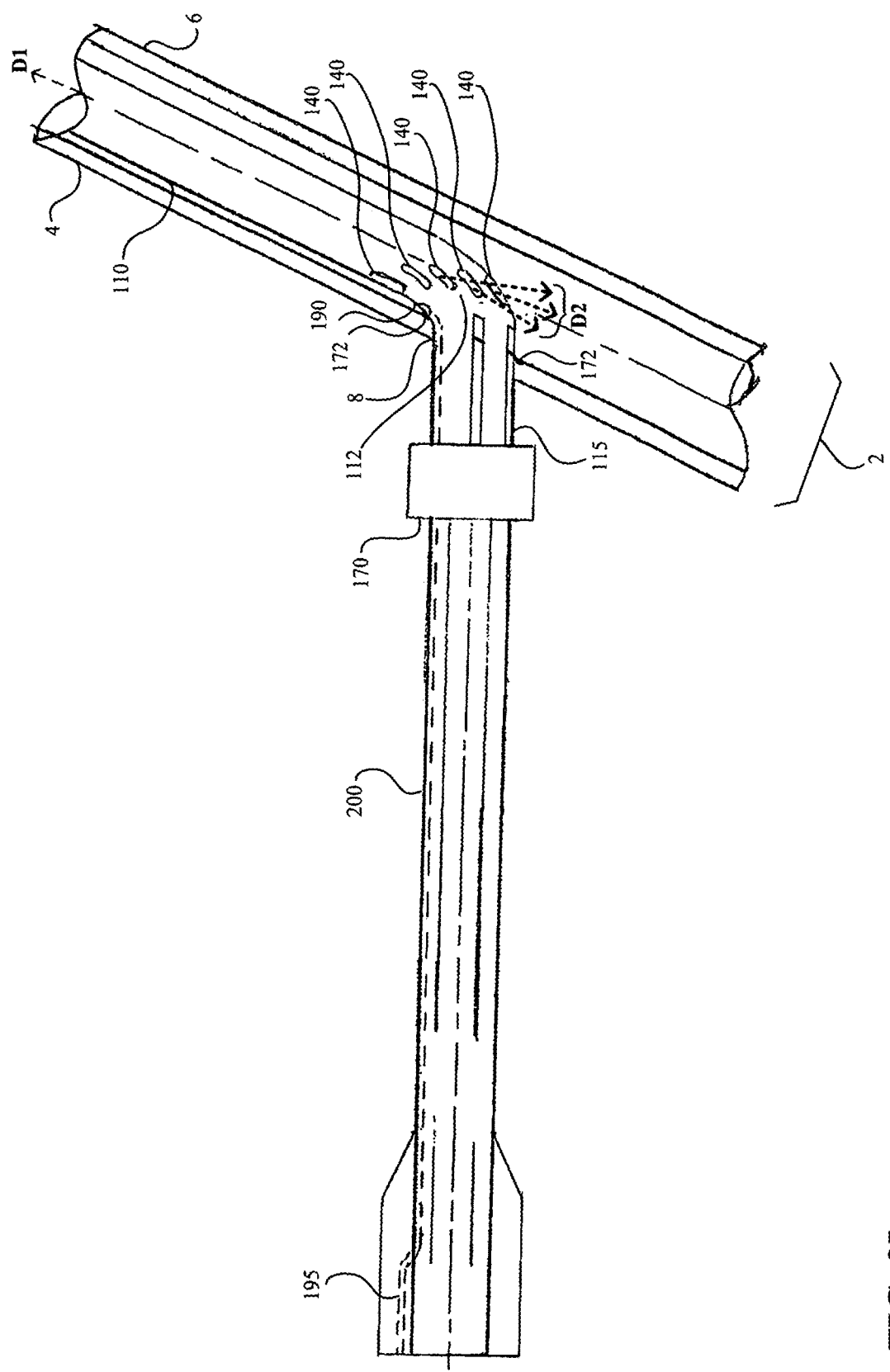

With reference to FIG. 3L, when the cannula is in use (i.e., after the vessel is cannulated/after the first segment 110 of the first tube 10 has been inserted into a patient or subject such that blood and/or another fluid can flow or is flowing from the first tube's distal opening 220 toward its proximal exit opening 120 and out of the fenestrations 140 and the proximal exit opening 120), the first segment 110 is configured to reside entirely within the vessel. The second segment 115 and the second portion 200 are configured to almost or essentially entirely reside external to the vessel, outside of the patient's body. For instance, when the cannula is in use, only a small portion of the second segment 115 that is distal to the anchoring element(s) provided by the anchoring assembly 150 and which is very near or adjacent to the inner surface of the cannulated vessel's superficial wall resides within the vessel. The first segment 100 is flexible or pliable along portions of its length, and the second segment 200 is at least generally or somewhat flexible or pliable along portions of its length. A lower or downward facing/downward oriented side of the first tube 10 can be longer than the corresponding upper or upward facing/upward oriented side of the first tube 10 to facilitate an appropriate/predetermined amount of curvature or bending for positioning the first tube 10 in a vessel 2, where "lower"/"downward facing"/"downward oriented" refer to portions of the first segment 110 that are opposite to and face away from the site or point at which the first segment 110 entered into the vessel, and which face away from the vessel's superficial wall 4.

In association with procedures such as heart lung bypass, cardio pulmonary bypass, ECMO, or essentially any other means of life support that requires the infusion of blood/fluid, the cannula structure of the present disclosure can be adapted to proximally infuse oxygenated blood into the body in a manner that maintains distal perfusion during the procedure(s). For instance, a first tube 10 in accordance with an embodiment of the present disclosure can be inserted into an artery (e.g., the right femoral artery) of a body extremity (e.g., the right leg, correspondingly). Blood supplied to the first tube's distal opening 220 can flow through the first tube 10 and simultaneously flow (a) out of the first tube's proximal exit opening 120 into the body (e.g., directed up the aorta towards the heart); and (b) out of the first tube's fenestrations 140, away from the body and into the cannulated extremity. Thus, blood leaving the first tube's proximal exit opening 120 flows along a first direction (e.g., proximal direction towards the heart), and blood leaving at least some of the first tube's fenestrations 140 flows along a set of directions different from or opposite to the first direction (e.g., distally away from the heart). As a result, the risk of ischemia in the extremity is substantially or greatly reduced, or essentially eliminated.

Aspects of Representative Fenestration Arrangements and Fenestration Embodiments The fenestrations 140 can be disposed along predetermined portions of the length of the first tube 10 and around or about predetermined portions of the circumference of first tube 10 in one or more manners depending upon embodiment details. In several embodiments, at least two fenestrations 140, each fenestration 140, or at least two subsets of fenestrations 140 are disposed in an oblique arrangement relative to the axial direction of the first segment 110 of the first tube 10, and/or a given fluid flow direction therethrough such as the first/primary fluid flow direction. Representative oblique arrangements of fenestrations 140 about/along portions of the first tube's first segment 110 are illustrated for the embodiments shown in FIG. 2A-2D; FIG. 2F-2I; FIG. 2J-2L; and FIG. 2N, where such embodiments include anchoring assemblies 150 having a set of selectively pressurizable/expandable/inflatable elements (e.g., a set of pressurizable/expandable/inflatable cuffs 160 and/or flange members 162); and also in the embodiments shown in FIG. 3A-3I, where such embodiments include anchoring assemblies 150 having a set of slidably displaceable elements (e.g., a slidably displaceable switch 170 that selectively extends/retracts a plurality of petals 172).

Certain embodiments include fenestrations 140 that are disposed in a non-oblique arrangement about predetermined portions of the first segment's circumference, at a predetermined position or location along the length of the first segment 110. For instance, representative non-oblique arrangements of fenestrations 140 are illustrated for the embodiment shown in FIG. 2M, which includes an anchoring assembly 150 having a set of pressurizable/expandable/inflatable elements; and the embodiment shown in FIG. 3J-3K, which includes an anchoring assembly 150 having a set of slidably displaceable elements.

Representative Aspects of Oblique Fenestration Arrangements

In various embodiments a plurality of fenestrations 140 are disposed obliquely around portions of the first tube's circumference. More particularly, with reference to FIG. 2B, FIGS. 2H-2I, FIGS. 2J-2L, and FIGS. 3G-3H, a plane that extends or cuts through multiple fenestrations 140 or each fenestration 140 forms a non-parallel and non-perpendicular angle, i.e. an angle $\alpha$ that is neither a right angle nor a multiple of a right angle, with respect to the axial direction or a lengthwise/longitudinal axis of the first segment 110 of the first tube 10 or a fluid flow direction therethrough (e.g., the first/primary or proximal fluid flow direction). In other words, a plane through a midpoint or reference point of two or more fenestrations 140 (e.g., a predetermined outermost point or corner thereof) that intersects a centrally or peripherally defined longitudinal axis of the first tube's first segment 110 forms an angle $\alpha$ that is neither a right angle nor a multiple of a right angle with respect to the longitudinal axis of the first segment 110 or a fluid flow direction therethrough (e.g., the first/primary or proximal fluid flow direction) at the point of intersection. In several embodiments, the angle $\alpha$ formed by the plane of the set of fenestrations 140 is 45° relative to the axial direction or fluid flow direction of the first tube 10. It should be apparent to a person having ordinary skill in the relevant art that a variety of other angles $\alpha$ are possible, such as between 300 and 60°.

In some embodiments having an oblique arrangement of fenestrations 140 about and along portions of the first tube's first segment 110, two or more fenestrations 140 need not be disposed on a plane in a linear manner relative to each other; rather, two or more fenestrations 140 can be disposed in a helical or spiral arrangement along and about the first segment 110. Consequently, a projection of a helical/spiral curve corresponding to the locations of the fenestrations 140 onto the first segment's longitudinal axis forms an oblique angle $\alpha$ that is neither a right angle nor a multiple of a right angle with respect to this longitudinal axis.

An oblique arrangement of fenestrations 140 can advantageously allow for more streamlined and/or effective distal flow of blood/fluid out of the fenestrations 140 as compared to a non-oblique arrangement, thereby enhancing or improving the efficiency of distal blood/fluid flow towards the patient's extremities and limbs. Additionally, an oblique arrangement of fenestrations 140 can result in enhanced structural integrity of the first segment 110 of the first tube 10 compared to a non-oblique fenestration arrangement, depending upon the number of fenestrations 140 carried by the first segment 110.

Representative Aspects of Non-Oblique Fenestration Arrangements

Specific embodiments in accordance with the present disclosure exhibit a non-oblique arrangement of at least some fenestrations 140. FIG. 2M and FIG. 3J-3K illustrate representative non-oblique or perpendicular fenestration arrangements, in which an angle α formed by a plane through the set of fenestrations 140 equals 90° relative to the lengthwise/longitudinal axis of the first segment 110 of the first tube 10 or the proximal fluid flow direction therethrough.

It should be noted that in certain embodiments, a plurality of fenestrations 140 (e.g., at least one pair of fenestrations 140) can be disposed non-obliquely about the first segment 110 at a given location thereon, while other fenestrations 140 or the overall/complete set of fenestrations 140 exhibit an oblique arrangement about and along portions of the first segment's length. Thus, in specific embodiments, a complete set of fenestrations 140 can include a plurality of fenestrations 140 disposed in a non-oblique arrangement, as well as a plurality of fenestrations disposed in an oblique arrangement with respect to the lengthwise axis of the first segment 110 of the first tube 10 and/or a fluid flow direction (e.g., the proximal fluid flow direction) therethrough.

Representative Aspects of Fenestration Positions and Dimensions

Fenestrations 140 can be disposed about or around the periphery, cross-sectional area, or circumference of the first segment 110 of the first tube 10 in a variety of manners in embodiments that exhibit non-oblique or oblique fenestration arrangements. In some embodiments, fenestrations 140 reside in each of a first or upper half of the first segment's cross-sectional area and a second or lower half of the first segment's cross-sectional area; however, in other embodiments, fenestrations 140 reside or approximately reside only in a particular half (e.g., the lower half) of the first segment's cross-sectional area. In addition, depending upon embodiment details, each fenestration 140 can have an identical cross-sectional area and/or shape, or some fenestrations 140 can have different cross-sectional areas and/or shapes relative to other fenestrations 140 (e.g., particular fenestrations 140 can have different dimensions compared to one or more other fenestrations 140).

Figure 4A:
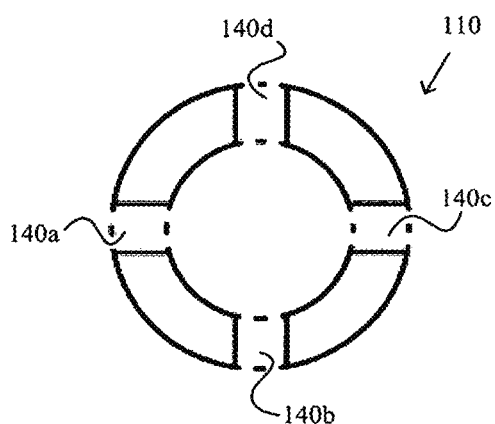
FIGS. 4A-4D are schematic illustrations of representative fenestration arrangements relative to a periphery, cross-sectional area, or circumference of a first segment of a catheter in accordance with particular embodiments of the present disclosure.

FIG. 4A-4D are schematic illustrations showing representative manners in which fenestrations 140 can be disposed relative to a cross-sectional area (e.g., a transverse or perpendicular cross-sectional area), periphery, or circumference of the first segment 110 of the first tube 10. As shown in FIG. 4A, in some embodiments, a first through a fourth fenestration 140a-d are uniformly disposed relative to the entire periphery of the first tube's first segment 110. However, in other embodiments, such as the representative embodiments shown in FIG. 4B-4D, fenestrations 140 are only partially disposed relative to the entire periphery of the first segment 110, such as along, or at a particular fraction or section of the first segment's cross-sectional area, periphery, or circumference.

Figure 4B:
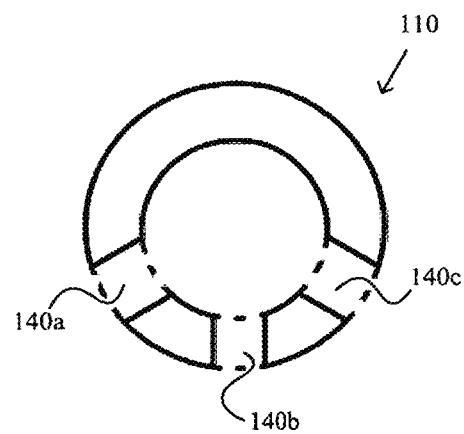
Figure 4C:
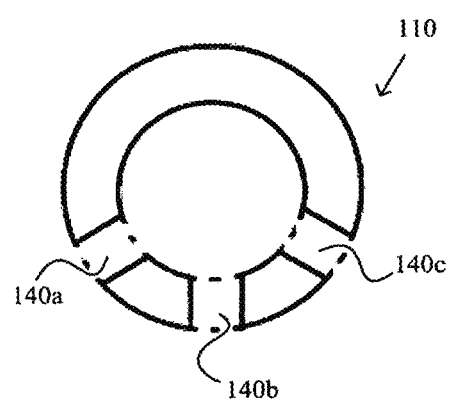
Figure 4D:
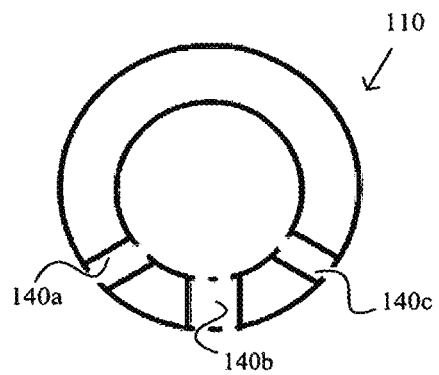

For purpose of simplicity and to aid understanding, in FIG. 4B-4D the set of fenestrations 140 include a first through a third fenestration 140a-c that are not disposed uniformly relative to or around the entire cross-sectional area, periphery, or circumference of the first segment 110. Rather, the arrangement of fenestrations 140 is such that (a) approximately or up to at most half of the cross-sectional area, periphery, or circumference of the first segment 110 carries fenestrations 140, such as a lower or downward facing/downward oriented half of the first segment's cross-sectional area, periphery, or circumference, where lower/downward facing/downward oriented are defined in a manner identical or analogous to that described above; and (b) other portions of the first segment's cross-sectional area, periphery, or circumference do not carry fenestrations 140.

For instance, the first fenestration 140a can be disposed at or approximately at a lower left portion of the cross-sectional area or circumference of the first segment's lower half; the second fenestration 140b can be disposed at or approximately at a bottom portion of the cross-sectional area or circumference of the first segment's lower half; and the third fenestration 140c can be disposed at or approximately at a lower right portion of the cross-sectional area or circumference of the first segment's lower half. The fenestrations 140a-c are thus carried by or disposed on (e.g., only carried by or disposed on) a lower or downwardly facing/downwardly oriented region of the lower half section of the cross-sectional area or circumference of the first tube's first segment 110, while other portions (e.g., the upper half) of the cross-sectional area or circumference of the first tube 10 exclude or do not contain fenestrations 140.

As mentioned above, in various embodiments the fenestrations 140 are obliquely disposed around a portion of the circumference of the first portion 110. After the cannula has been inserted into and anchored within a vessel, such fenestrations 140 are slightly or very slightly proximal or proximally adjacent/contiguous to the set of anchoring elements provided by the anchoring assembly 150. In a representative embodiment including three fenestrations 140a-c disposed in an oblique arrangement such as in a manner shown in FIG. 2H-2I or FIG. 2J-2L, the first fenestration 140a can be closest to the cannula's distal end 230, the second fenestration 140b can be proximal to the first fenestration 140a, and the third fenestration 140c can be proximal to the second fenestration 140b. Various other oblique arrangements of fenestrations 140 are possible, as will be readily recognized by an individual having ordinary skill in the relevant art.

With additional conceptual reference to FIG. 3L, if a cannula that includes fenestrations 140 carried on the upper half of the first segment's cross-sectional area, periphery, or circumference were inserted into a cannulation site or point 8 and anchored within a vessel 2, portions of at least some of the fenestrations 140 carried by this upper half section would face upward, toward the vessel's superficial wall 4. Distal blood/fluid flow through such fenestrations 140 is less efficient than for fenestrations 140 that at least partially face in a downward generally downward, or at least somewhat downward direction, away from the cannulation site, and/or which at least partially face in a distal direction. By limiting the positions of fenestrations 140 to approximately or at most a lower half of the cross-sectional area, periphery, or circumference of the first tube's first segment 110, and in particular lower portions of the lower half of the cross-sectional area, periphery, or circumference of the first segment 110, blood/fluid flow out of the set of fenestrations 140 in the distal direction away from the heart is increased and/or more efficient. Furthermore, such an arrangement of fenestrations 140 in only a particular half (e.g., the lower half) or region of the first segment 110 can enhance the structural integrity of the first segment 110, as there are fewer openings therein that can reduce the first segment's structural integrity.

It will be apparent to an individual having ordinary skill in the relevant art that the number of fenestrations 140 disposed in a predetermined half-portion of the first tube's cross-sectional area, periphery, or circumference is not limited to three; there can be fewer than or more than three fenestrations 140 disposed in such a manner. It will be apparent to such an individual that the fenestrations 140 can also be arranged to reside around more than a half portion of the cross-sectional area, periphery, or circumference of the first segment 110, such as three-quarters thereof, depending upon embodiment details.

Each fenestration 140 is configured or adapted to provide an intended shape, size, or blood/fluid communication area, and not all fenestrations 140 need to have an identical shape, size, or blood/fluid communication area as indicated in FIGS. 4B and 4D. The shape(s) and/or dimension(s) of particular fenestrations 140 can be defined relative to the shape(s) and/or dimension(s) of other fenestrations 140 carried by the first segment 110 (e.g., made larger or smaller, depending upon the position(s) of certain fenestrations 140 relative to other fenestrations 140) in order to provide a cannula in accordance with an embodiment of the present disclosure with an intended distal blood/fluid flow or output relative to an expected proximal blood/fluid flow or output, and/or an intended, target, or desired degree of structural integrity. In a representative embodiment, a ratio of a total fenestration area through which blood/fluid can exit the fenestrations 140 (e.g., a total cross sectional area for blood/fluid flow provided by the fenestrations 140) to a total proximal exit opening area through which blood/fluid can exit the first tube's proximal exit opening 120 is not less than 10% and typically between 10% to 40% (e.g., 20% to 40%, 25% to 35%, or 30%).

Aspects of Representative Anchoring Assemblies and Anchoring Elements

Fluid Pressurizable/Expandable/Inflatable Anchoring Assemblies

In multiple embodiments such as shown in FIG. 2A-2N, the anchoring assembly 150 includes a pressurizable/expandable/inflatable cuff 160 and/or one or more flange portions, sections, elements, structures, or members 162 that serve as anchoring elements by which the fenestrations 140 and the proximal end opening 120 of the first segment 110 are retained or maintained in an intended position within the vessel.

Figure 2C:
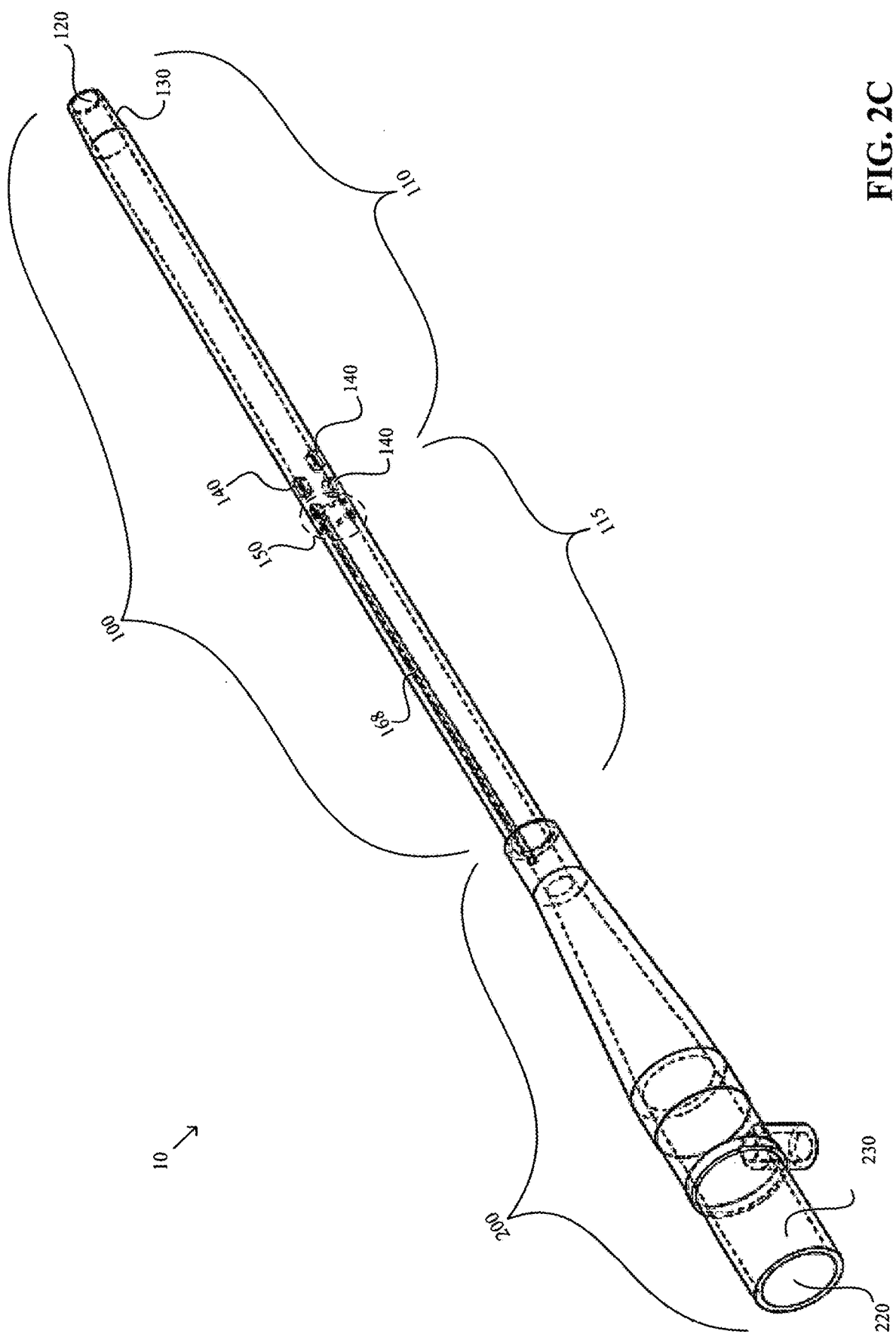
FIG. 2A-2N illustrate aspects of representative catheters that include anchoring assemblies having at least one pressurizable/expandable/inflatable elements in accordance with particular embodiments of the present disclosure.
Figure 2D:
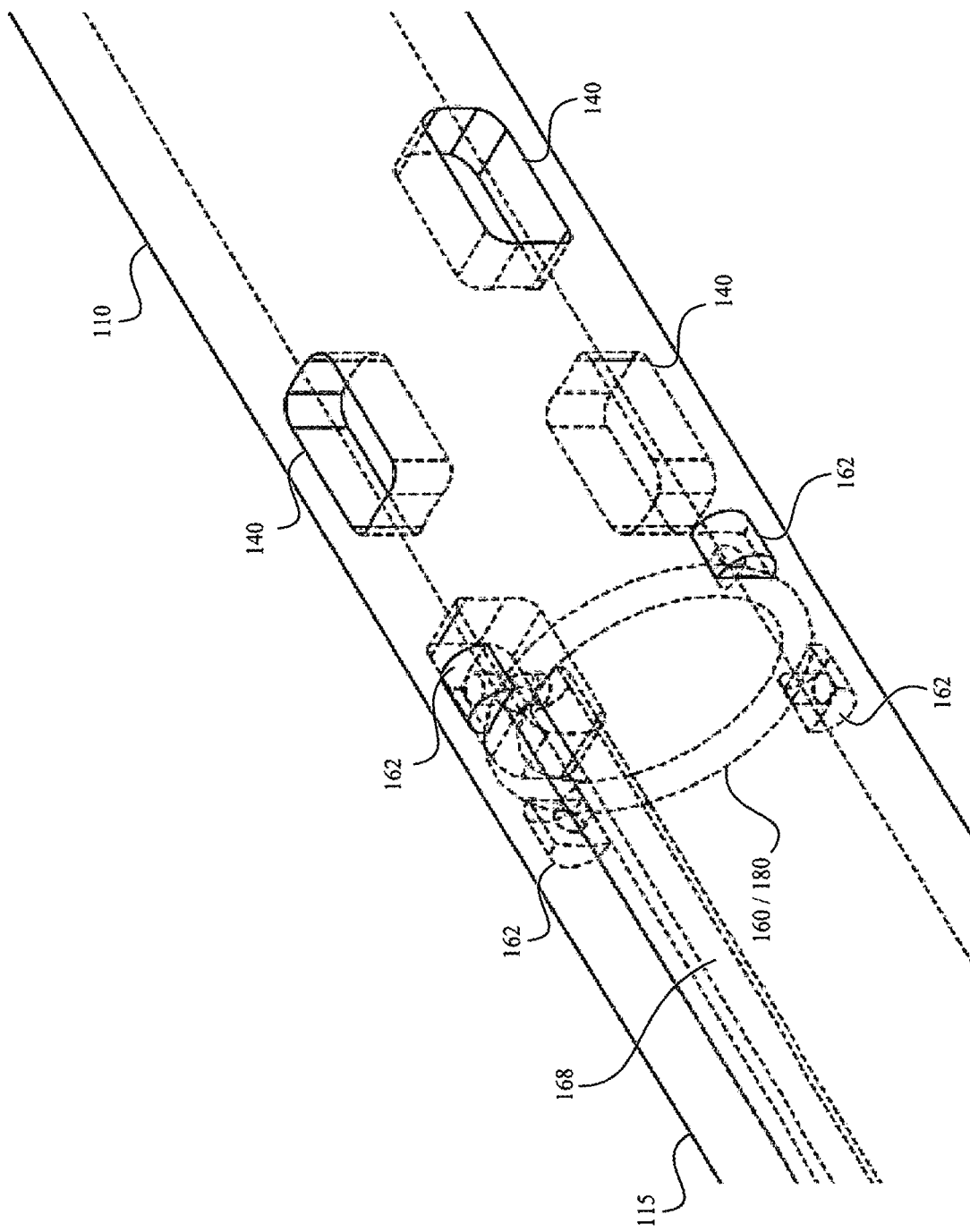

For instance, FIG. 2A-2D illustrate a representative first embodiment of a cannula having an anchoring assembly 150 that includes an expandable cuff 160 carrying and/or fluidically coupled to a plurality of anchor members 162 in accordance with the present disclosure. More particularly, FIG. 2A provides a representative external perspective view of this first cannula embodiment; FIG. 2B provides a representative plan view along portions of the first portion 100 of this cannula's first tube 10; FIG. 2C provides a representative interior or internal perspective view of this first cannula embodiment; and FIG. 2D provides a magnified isometric internal schematic illustration of the anchoring assembly 150 in this first cannula embodiment.

In such an embodiment, the flange members 162 are configured to radially/outwardly protrude through small openings or slots formed in the first portion 100 of the first tube 10 in response to pressurization/expansion/inflation of the cuff 160, such that the flange members 162 extend slightly beyond the exterior surface of the first segment 110 as the cuff 160 is pressurized/expanded/inflated, while the cuff 160 is disposed and remains internal to the exterior surface of the first segment 110. Thus, from an external view, the cuff 160 remains hidden beneath the exterior surface of the first tube 10, as indicated in FIGS. 2A and 2B. Rather, only the anchoring assembly's flange members 162 selectively protrude away from and beyond the exterior surface of the first portion 100 of the first tube 10 as a result of pressurization/expansion/inflation of the cuff 160, whereas the anchoring assembly's cuff 160 remains internal to the exterior or outer surface of the first portion 100 of the first tube 10.

Figure 2E:
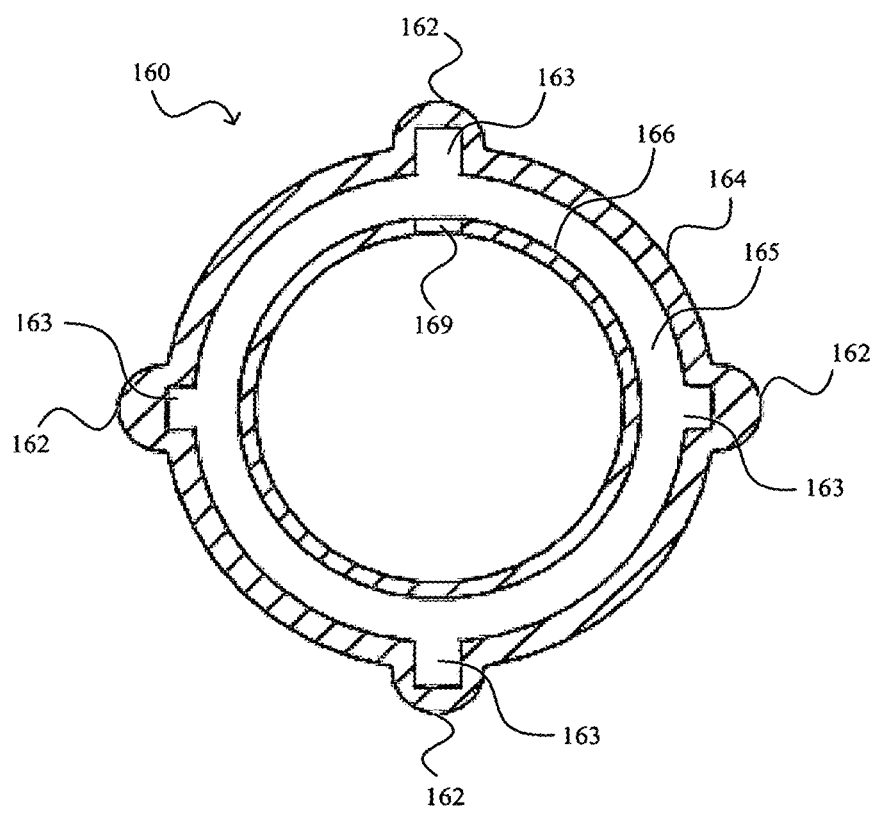
Figure 2J:
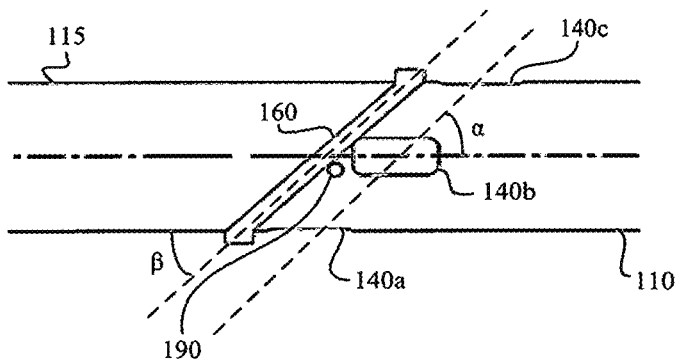
Figure 2K:
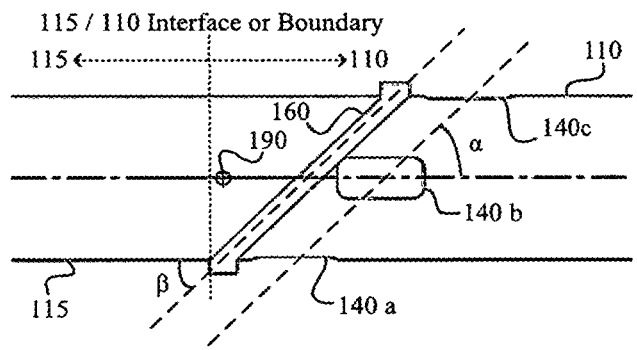
Figure 2L:
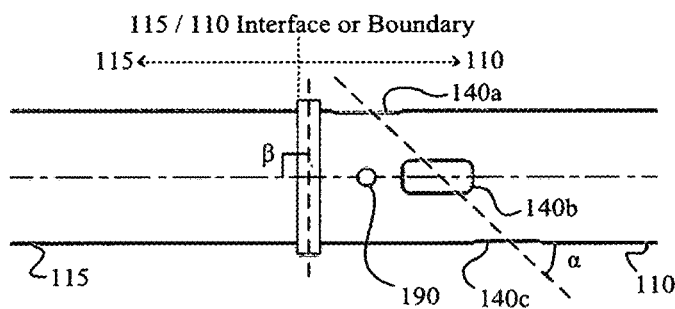
Figure 2M:
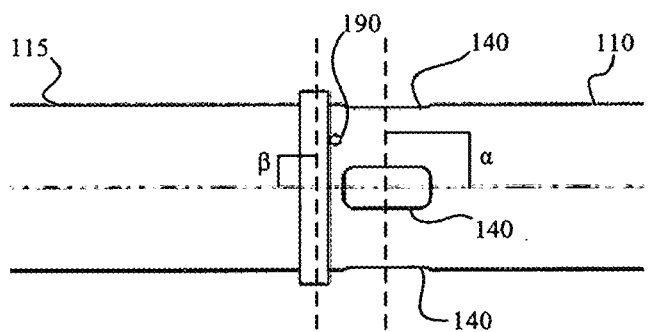
Figure 2N:
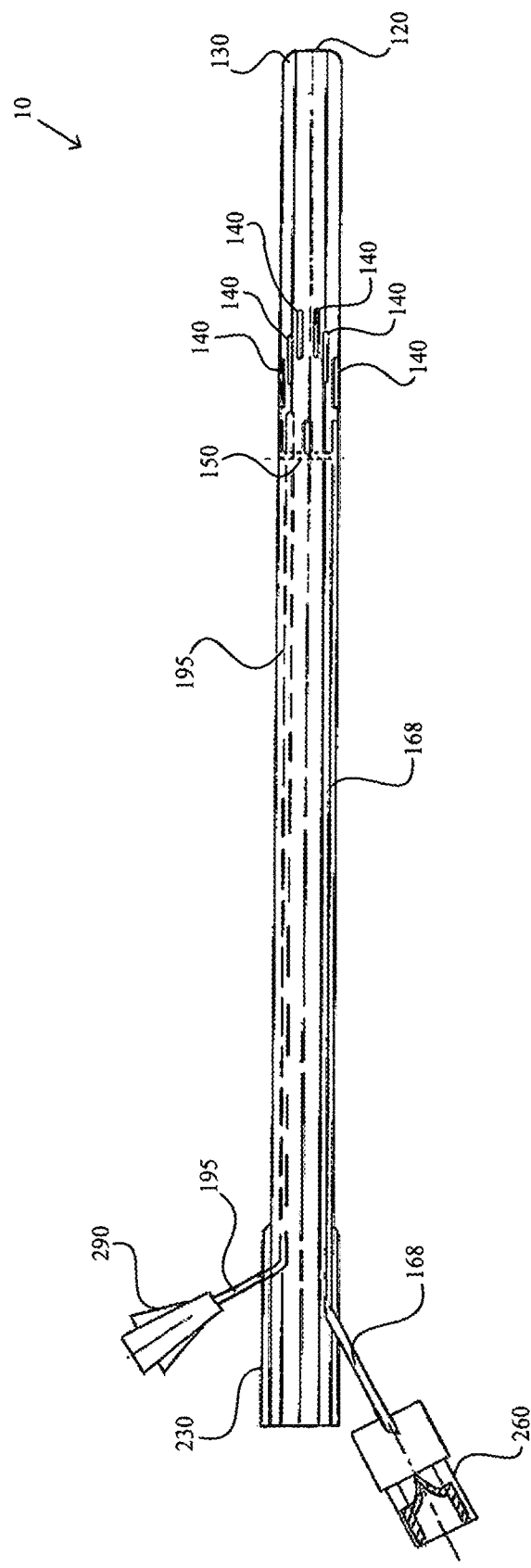

As shown in FIG. 2C and more clearly shown in FIG. 2D, the cuff 160 in this first cannula embodiment resides and is retained beneath the exterior surface of the first tube 10, for instance, circumferentially disposed within or at least partially within portions of the thickness of the wall of the first portion 100 of the first tube 10, in a manner that avoids or substantially avoids adversely affecting blood/fluid flow through the lumen(s) of the first tube 10. When pressurized/expanded/inflated, the cuff 160 can reinforce or aid the structural integrity of the first portion 100 of the first tube 10. As indicated in FIG. 2D, the cuff 160 is fluidically coupled to a cuff pressurization/expansion/inflation tube 168 that is fluidically couplable or coupled to a source of pressurized gas or liquid (e.g., air) by which the cuff 160 can be pressurized/expanded/inflated and the flange members 162 can correspondingly be displaced outward beyond the exterior surface of the first portion 100 of the first tube 10. FIG. 2E is a cross-sectional illustration of a representative cuff 160 and corresponding flange members 162 according to an embodiment of the present disclosure. In an embodiment, the cuff 160 includes or is a generally elliptical or circular ring or sleeve type structure having an outer surface or layer 164, an inner surface or layer 166, and a chamber or cavity 165 therebetween. The outer layer 164 is expandable in response to the delivery of positive fluid pressure (e.g., air or liquid pressure) into the cavity 165. The cavity 165 is fluidically coupled to the cuff pressurization/expansion/inflation tube 168 by way of at least one activation port 169.

The flange members 162 can be integrally carried by or formed from portions of the cuff's outer layer 164, or structurally and/or fluidically coupled to or formed from portions of the cuff's outer layer 164. For instance, the cuff's outer layer 164 can be shaped such that the cavity 165 includes a plurality of outwardly or radially directed extensions 163 therein, above which the flange members 162 reside. Pressurization/inflation of the chamber 165 results in outward expansion of the cuff's outer layer 164 away from its inner layer 166 and hence away from the interior or first lumen of the first segment 110, resulting in outward or radial expansion or displacement of the chamber's extensions 163 and the flange members 162 away from the first lumen of the first segment 110, toward and slightly beyond the exterior surface of the first segment 110. Analogously, appropriate depressurization/deflation of the chamber 165 results in inward contraction of the cuff's outer layer 164 toward its inner layer 166 and the first lumen of the first segment 110, resulting in radial contraction or inward displacement of the extensions 163 and the flange members 162 toward the first lumen of the first segment 110 until the outermost surfaces of the flange members 162 are disposed below the exterior surface of the first segment 110.

The outward or radial extent or height of each extension 163 and/or the thickness of those portions of the cuff's outer layer 164 that form the flange members 162 can be selected as required to facilitate or enable reliable retention or anchoring of the cannula in the vessel. In relation to the first segment 110 having a predefined diameter suitably dimensioned according to the patient's vessel size, the maximum cross-sectional area or diameter provided by the activated or outwardly expanded flange members 162 can be approximately 10% to 30% larger (e.g., about 15%-25% larger) than the cross-sectional area or external diameter of the first segment 110. A person having ordinary skill in the relevant art will understand that the extent or height to which the flange members 162 extend beyond the outer surface of the first segment 110 can vary according to embodiment details and/or the nature and/or size of the vessel under consideration. For instance, in a representative embodiment in which the first segment has a diameter of 21 French, complete pressurization/expansion/inflation of the cuff 160 results in the radially outermost surfaces of the flange members 162 being disposed a distance of approximately 1.5 mm away from the exterior surface of the first segment 100. While the embodiment shown in FIG. 2E includes four flange members 162a-d, other embodiments can include additional or fewer flange members 162, in a manner readily understood by an individual having ordinary skill in the relevant art.

In the first cannula embodiment shown in FIG. 2A-2D, the fenestrations 140 are disposed in an oblique arrangement relative to the lengthwise/longitudinal axis of the first segment 100 or a blood/fluid flow direction therethrough, whereas the flange members 162 are disposed in a non-oblique arrangement relative to the lengthwise/longitudinal axis of the first segment 100 or a blood/fluid flow direction therethrough. In some embodiments, the flange members 162 can be disposed in an oblique arrangement in a manner analogous to that described above with respect to the fenestrations 140, as further detailed hereafter.

FIG. 2F-2I illustrate a representative second embodiment of a cannula in accordance with the present disclosure, which has an anchoring assembly 150 that includes an expandable cuff 160 which is fluidically coupled to a plurality of flange members 162 that are obliquely arranged relative to the lengthwise/longitudinal axis of the first segment 110 or a blood/fluid flow direction therethrough. More particularly, FIG. 2F provides a representative external perspective view of this second cannula embodiment; FIG. 2G provides a representative magnified view of portions of FIG. 2F; FIG. 2H provides a representative internal view corresponding to FIG. 2G; and FIG. 2I provides a representative cross-sectional view corresponding to FIG. 2H.

In an oblique arrangement of flange members 162, a plane that extends or cuts through multiple flange members 162 or each flange member 162 forms a non-parallel and non-perpendicular angle, i.e., an angle θ that is neither a right angle nor a multiple of a right angle, with respect to the axial direction or a lengthwise/longitudinal axis of the first segment 110 of the first tube 10 or a fluid flow direction therethrough (e.g., the first/primary or proximal fluid flow direction). In other words, a plane through a midpoint or reference point of two or more flange members 162 (e.g., a predetermined outermost point or corner thereof) that intersects a centrally or peripherally defined longitudinal axis of the first tube's first segment 110 forms an angle θ that is neither a right angle nor a multiple of a right angle with respect to the longitudinal axis of the first segment 110 or a fluid flow direction therethrough. An oblique arrangement of flange members 162 can enable activated or fully deployed flange members 162 to be in a more planar orientation relative to the superficial wall of the cannulated vessel when the cannula is in use. This in turn can provide a more effective abutment or anchoring of the flange members 162 on the superficial wall, thereby aiding robust or reliable retention or anchoring of the first segment 110 within the cannulated vessel. The angle θ can be the same as or different than the angle α, depending upon embodiment details, as will be readily understood by an individual having ordinary skill in the relevant art.

As illustrated in FIGS. 2F, 2H, and 2I, in this embodiment the cuff 160 is structurally separate or distinct from or non-integral with at least some of the flange members 162. For purpose of simplicity and to aid understanding, the representative second embodiment 162 includes a first through a third flange member 162a-c in an oblique arrangement, and a first through a third fenestration 140a-c in an oblique arrangement. The first flange member 162a is the distal-most flange member 162a; the second flange member 162b is disposed in a proximal direction away from the first flange member 162a; and the third flange member 162c is disposed in a proximal direction away from the second flange member 162b. Various other oblique arrangements of flange members 162 are possible, as will be readily understood by an individual having ordinary skill in the relevant art.

In an embodiment, the first flange member 162a is carried by or fluidically coupled to the cuff 160 (e.g., integrally formed with or as a portion of the cuff 160) in a manner essentially identical or analogous to that described above. For instance, the second flange member 162b can include a pressurizable/expandable/inflatable sleeve or channel that is fluidically coupled to the cuff 160 by way of a first fluid communication port/passage 161a. The third flange member 162c can also include a pressurizable/inflatable sleeve or passage, which is fluidically coupled to the second flange member 162b by way of a second fluid communication passage 161b. Each fluid communication passage 161a-b can reside or be formed in a portion of the thickness of the first segment's wall.

Pressurization/inflation of the cuff 160 results in pressurization of the first and second fluid communication passages 161a-b. Correspondingly, pressurization/inflation of the cuff 160 results in radial or outward expansion or displacement of the first through third flange members 162a-c away from the first lumen of the first segment 110, toward and slightly beyond the exterior surface of the first segment 110. Analogously, appropriate depressurization/deflation of the cuff 160 results in inward depressurization/deflation of the first and second fluid communication passages 161a-b. Correspondingly, depressurization/deflation of the cuff results in radial contraction or inward displacement of the flange members 162a-c toward the first lumen of the first segment 100 until the outermost surfaces of the flange members 162a-c are disposed flush with or below the exterior surface of the first segment 110.

As an alternative to the foregoing, in some embodiments the pressurizable/expandable/inflatable cuff 160 can simply be replaced by annular/elliptical/circular fluid transport channel or air channel 180, which is also shown in FIGS. 2D and 2F-2I. The annular air channel 180 itself can be a rigid or generally rigid structure, rather than an expandable structure. In such embodiments, the annular air channel 180 resides internal to the outer/exterior surface of the first portion 100 of the first tube 10 (e.g., within internal portions of the wall of the first portion 100), and is fluidically coupled to a plurality of pressurizable/expandable/inflatable flange members 162 by way of a set of fluid communication port/passages 161, such that the flange members 162 are selectively outwardly/radially displaceable or inwardly displaceable as a result of the application of positive pressure or negative pressure to the annular air channel 180, respectively.

It can be noted from the description above that in embodiments such as those shown in FIGS. 2A-2I, flange members 162 can be pressurized/expanded/inflated collectively, such as in a uniform or generally uniform manner for multiple or all flange members simultaneously; or in a sequenced/sequential manner, depending upon how positive pressure is communicated thereto (e.g., some flange members 162 may more fully or fully pressurize/expand/inflate before other flange members 162). Corresponding or analogous considerations apply to flange member depressurization/contraction/deflation as a result of the application of a negative pressure thereto.

In view of the embodiments shown in FIGS. 2A-2E and 2F-2I, flange members 162 can be pressurized/expanded/inflated and displaced beyond the exterior/outer surface, periphery, cross-sectional area, circumference, or diameter of the first portion 100 of the first tube 10 by way of pressurization/expansion/inflation of the cuff 160, such as through the introduction of air (or other type of fluid) into the cuff 160 from the cuff pressurization/expansion/inflation tube 168. Such flange members 162 can be referred to as activated flange members 162. For instance, air can be introduced by a user such as a clinician by applying a positive air pressure to a one-way valve assembly 260 (which can include more than a single one-way valve structure) disposed within the lumen of the first tube 10. A one-way valve assembly 260 can include or be, for instance, a duck-bill valve assembly such as illustrated in FIG. 2N.

As a result of radial displacement beyond the exterior surface of the first tube's first portion 100, the activated flange members 162 provide or define a cross-sectional area, circumference, or diameter that is larger than an outer cross sectional, circumference, or diameter area of the first segment 110 at a location around the first segment 110 at which the flange members 162 are disposed. The activated flange members 162 can subsequently abut or anchor to the internal surface or superficial wall of the cannulated vessel, thereby aiding fixation, retention, or maintenance of the first segment 110 and the fenestrations 140 and proximal end opening 120 thereof at a predictable or intended position within the cannulated vessel. In order to retract the cannula, the user/clinician can apply a negative pressure to or deactivate the one-way valve assembly 260 that is sufficient to overcome the valve assembly's one-way flow behavior, such that the cuff 160 depressurizes/contracts/deflates/collapses to its minimal volume or near-minimal volume configuration or shape. Consequently, the user/clinician can safely retract or withdraw the cannula through the cannulation site 8.

In still further embodiments, the cuff 160 can be carried by an exterior or outer surface of the first segment 110 of the first tube 10, such as in a manner indicated in FIG. 2J-2M. The cuff 160 can include or be an annular structure, which can be contoured/tapered/flanged or unflanged, (e.g., the cuff 160 can include a set of flange(d) regions, structures, or members 162 thereon or thereabout). The orientation/position of the cuff 160 around the first portion 100 of the first tube 10, the shape or cross-sectional profile of the cuff 160, and/or the presence of flanged regions, structure, or members 162 on the cuff 160 can facilitate distal blood flow past the cuff 160 when the cuff 160 is activated or deployed within the vessel, such that the cuff 160 does not impede or completely impede blood/fluid flow within the vessel, especially when the cannula is accidentally advanced further into the vessel (i.e., deeper than an intended or ideal position).

In embodiments in which the cuff 160 is carried on the outer surface of the first segment 110, at the location(s) at which the first segment 110 carries the cuff 160 the thickness of the wall of the first segment 110 can be reduced such that the cross-sectional area corresponding to the cuff 160 (including its flange members 162) when the cuff 160 is depressurized/contracted/deflated is nearly, approximately, or essentially the same as that of the cross-sectional area of the first segment 110 adjacent to where the cuff 160 resides, thereby aiding smooth insertion of the first segment 110 into the vessel and smooth withdrawal therefrom.

As indicated in FIG. 2J-2K, in embodiments in which the cuff 160 is externally carried by the first segment 110, the cuff 160 can have an oblique orientation with respect to the lengthwise/longitudinal axis of the first segment 110 or a fluid flow direction therein. Consequently, a plane that extends or cuts through the cuff 160 forms a non-parallel and non-perpendicular angle, i.e. an angle 3 that is neither a right angle nor a multiple of a right angle, with respect to the axial direction or a lengthwise/longitudinal axis of the first segment 110 of the first tube 10 or a fluid flow direction therethrough (e.g., the first/primary or proximal fluid flow direction), in a manner analogous to that described above. Alternatively, as indicated in FIG. 2L-2M, the cuff 160 can have a non-oblique orientation with respect to the first segment's lengthwise/longitudinal axis or a fluid flow direction therein, such that the angle β equals 90°.

Slidably Displaceable Anchoring Assemblies and Elements

In alternative embodiments, the anchoring assembly 150 can include slidably displaceable structures by which anchoring elements such as a plurality of petals 172 can expand outwardly or radially away from the first segment 110 and abut or anchor on the inside surface of the cannulated vessel. The following description provides details directed to particular representative embodiments of such anchoring assemblies 150.

Figure 3M:
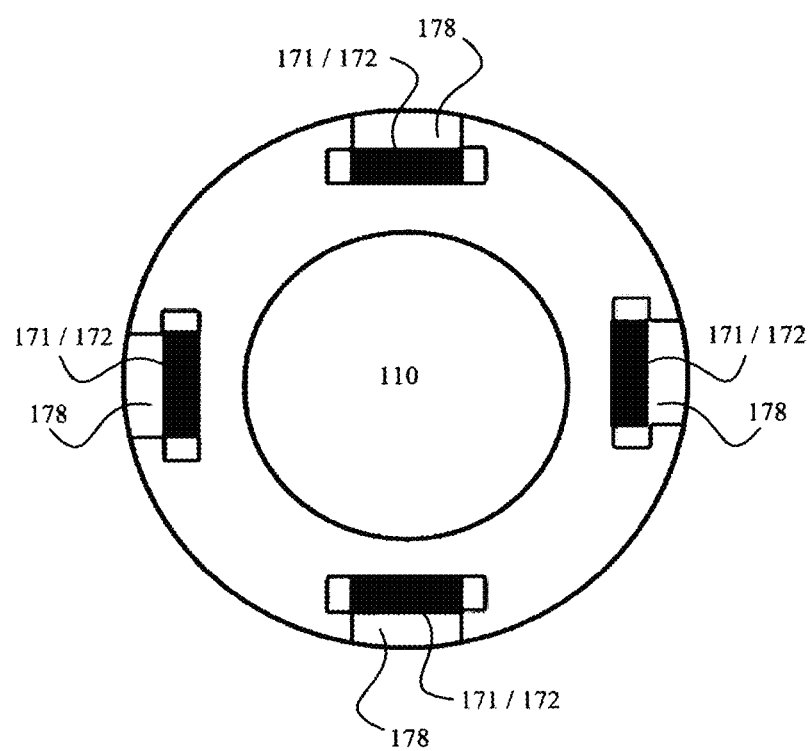

FIG. 3A is a representative perspective external view, FIG. 3B is a representative perspective internal view, FIG. 3C is a representative plan view, and FIG. 3D is a representative cross sectional view of a cannula that includes an anchoring assembly 150 having slidably displaceable elements in accordance with an embodiment of the present disclosure. Additionally, FIG. 3E is a representative magnified internal view showing such an anchoring assembly 150 in an inactivated state, and FIG. 3F is a representative magnified internal view showing this anchoring assembly 150 in an activated state. Furthermore, FIG. 3G is a representative magnified plan view and FIG. 3H is a representative magnified cross sectional view of such an anchoring assembly 150. FIG. 3I is a representative magnified perspective view of a cannula that includes an anchoring assembly 150 having slidably displaceable elements in accordance with another embodiment of the present disclosure; and FIGS. 3J and 3K are representative magnified cross-sectional views of a cannula that includes an anchoring assembly 150 having slidably displaceable elements in accordance with a further embodiment of the present disclosure. FIG. 3L is a representative internal view showing a cannula that includes an anchoring assembly 150 having slidably displaceable elements after insertion into a vessel in accordance with an embodiment of the present disclosure. Finally, FIG. 3M is a cross-sectional view of slidably displaceable elements/structures/elongate pieces of thin flexible material disposed within passages that extend along sections of the wall of the first portion 100 of the first tube 10, which correspond to or form outwardly or radially extendable and inwardly retractable petals 172, in accordance with an embodiment of the present disclosure.

In embodiments such as those shown in FIG. 3A-3L, the anchoring assembly 150 includes a slidable structure 170 such as a slidably displaceable switch or activation element that is mechanically coupled to the set of petals 172. The set of petals 172 can include, be coupled to, or be formed from portions (e.g., end or tip portions) of thin metal or polymer/plastic strips 171 (or any other significantly or highly flexible/pliable biocompatible material) that are disposed along and within the wall of the first portion 100 of the first tube 10, terminating just distal to the fenestrations 140. A corresponding set of slits or recesses and/or an intentionally formed defect or petal exit point in the wall (e.g., a thin and/or puncturable region of the wall) just distal to the set of fenestrations 140 (e.g., distally adjacent or approximately adjacent to the fenestrations 140) enables the petals 172 to protrude or extend outwardly beyond the outer surface of the first segment 110 in response to activation of the switch 170, that is, displacement of the switch 170 in the proximal direction, allowing at least some of the petals 172 to anchor to the superficial wall of the cannulated vessel. The terminal end portions or ends of the petals 172 can be blunt or curved in order to minimize the risk of damaging the vessel, in a manner readily understood by an individual having ordinary skill in the relevant art. Additionally, depending upon embodiment details, the some or each of the petals 172 can exit or protrude from the first segment 110 at an angle of approximately or nearly 90° with respect to the outer/exterior surface of the first segment 110, or another angle, such as within 15°-30° of perpendicular to the outer/exterior surface of the first segment 110.

FIGS. 3B, 3D, 3E, 3F, 3H, and 3K illustrate thin strips of material 171 (e.g., metal or plastic) disposed along and within portions of the wall(s) of the first portion 100 of the first tube 10 in accordance with an embodiment of the present disclosure. FIG. 3M is a cross-sectional illustration of the first portion 100 of the first tube 10, illustrating thin strips 171 disposed in slots 178 formed in the first portion's walls in accordance with an embodiment of the present disclosure. Distal sections of the strips 171 are securely coupled to the switch 170, such that the strips 171 can be selectively displaced in a proximal or distal direction, subject to physically imposed switch displacement limits, in response to respective proximal or distal displacement of the switch 170. In various embodiments, the proximal ends/tips of the strips 171 form the petals 172 after (a) the switch 170 has been displaced in a proximal direction; (b) the strips 171 have correspondingly been displaced in the proximal direction; and (c) the proximal ends/tips of the strips 171 protrude or extend outwardly or radially away from the exterior surface of the first segment 110 by a predetermined distance.

The switch 170 is configured to slide along the first tube 10, specifically the second segment 115 thereof. In some embodiments, the second segment 115 and the switch 170 include male and female structures that engage with each other and which facilitate control of switch displacement. For instance, the second segment 115 can include a set of grooves or channels formed therein that match a set of teeth or bumps carried by the switch 170. The set of grooves encircles a portion of the second segment 115, and the set of bumps are disposed along portions of the inner diameter and length of the switch 170. Each groove coincides with a bump. The set of grooves can resemble the threading of a screw, while the set of bumps can resemble the threading of a nut. The user or clinician can push the switch 170 towards the cannula's proximal end 130 to activate the petals 172. Stepwise advancement of the switch 170 can cause interaction between the bumps and the grooves in a manner that creates a frictional force that prevents the switch 170 from sliding backwards (i.e. distally) to its original position. Alternatively, the second segment 115 can have a set of bumps and the switch 170 can have a corresponding set of grooves.

FIGS. 3A, 3C, 3D, 3F, 3H, 3I, and 3K show petals 172 that extended outwardly in directions away from the axis of the first lumen of the first segment 110 and beyond the first segment's exterior surface or cross-sectional area following user/clinician activation of the switch 170. While the embodiments shown include three or four petals 172, other embodiments can include additional or fewer petals 172, in a manner readily understood by an individual having ordinary skill in the relevant art. In general, the anchor assembly 150 is suitably structured such that there are at least two petals 172 that can act as anchoring points for retaining or anchoring the first segment 110 at an intended position within the cannulated vessel.

In an embodiment having three petals 172, the petals 172 and their corresponding strips 171 can be uniformly separated from each other about the entire periphery/circumference of the second segment 110 by 120 degrees. In a representative embodiment having four petals 172 such as that shown in FIG. 3M, the petals 172 and their corresponding strips 171 can be uniformly separated from each other about the entire periphery/circumference of the second segment 110 by 90 degrees. Other arrangements of petals 172 are also possible, as will be readily understood by an individual having ordinary skill in the relevant art.

With further reference to FIG. 3M, each strip 171 resides in a corresponding slot 178 that extends along a fraction of the length of the first tube 10. One or more types of fluid impermeable barriers can reside within the slots 178 in order to prevent the backflow of blood/fluid therethrough when the petals 172 are activated/deployed. For instance, one or more slots 178 can include a compressible foam material (e.g., an open cell and/or closed cell foam material) that extends along a predetermined short or generally short length of the slot 178 (e.g., a few to several millimeters, or up to 1 centimeter), which fills those portions of the cross sectional area of the slot 178 that are not occupied by a strip 171, and which provides a fluid impermeable barrier or seal between the inner walls of the slot 178 and the outer periphery of the strip 171 disposed therein. Such a foam material can be disposed along one or more sections of a given slot 178, such as slightly distal to the terminal end of the strip 171 that defines the petal 172 thereof, and/or slightly proximal to a switch displacement limit/stop structure. Alternatively or additionally, a strip 171 can carry a set of bumps, kinks, or ridges that occupy the internal cross-sectional area of its corresponding slot 178, and which serve as fluid flow barriers within the slot 178.

In a manner essentially identical or analogous to that described above for the flange members 162, the outward or radial extent or height of each petal 172 can be defined or selected as required to facilitate or enable reliable retention or anchoring of the cannula in the vessel. In relation to the first segment 110 having a predefined diameter suitably dimensioned according to the patient's vessel size, the maximum cross-sectional area or diameter provided or defined by the activated or outwardly expanded petals 172 can be approximately 10% to 30% larger (e.g., about 15%-25% larger) than the cross-sectional area or external diameter of the first segment 110. A person having ordinary skill in the relevant art will understand that the extent or height to which the petals 172 extend beyond the outer surface of the first segment 110 can vary according to embodiment details and/or the nature and/or size of the vessel under consideration. For instance, in a representative embodiment in which the first segment has a diameter of 21 French, complete activation or maximum outward/radial displacement of the petals 172 results in the radially outermost surfaces of the petals 172 being disposed a distance of approximately 1.5 mm away from the exterior surface of the first segment 100.

In a manner also essentially identical or analogous to that described above, the petals 172 can be arranged obliquely or non-obliquely/perpendicularly with respect to the axial or fluid flow direction of the first segment 110. In an oblique arrangement, a plane in which two or more petals 172 reside forms a non-parallel and non-perpendicular angle $\alpha$, i.e. an angle that is neither a right angle nor a multiple of a right angle, with respect to a lengthwise/longitudinal axis of the first segment 110 and/or a fluid flow direction therein. In one embodiment, the angle $\alpha$ is 45°; however, it will be apparent to the person having ordinary skill in the relevant art that other angles $\alpha$ are possible, such as between 30° and 60°. The effects or advantages of an oblique arrangement of petals 172 is analogous or essentially identical to the effects or advantages of an oblique arrangement of flange members 162. Individual petals 172 can be positioned in various manners in embodiments having an oblique petal arrangement. For instance, in one oblique arrangement such as that shown in FIG. 3I, a first petal 172a can be positioned closest to the cannula's distal end 230, a third petal 172c can be positioned furthest from the distal end 230, and a second petal 172b can be positioned between the first petal 172a and the third petal 172c.

In a non-oblique/perpendicular arrangement, a plane in which two or more petals 172 reside forms a perpendicular angle $\alpha$ with respect to the lengthwise/longitudinal axis of the first segment 110 and/or a fluid flow direction therein. In specific embodiments, the first segment 110 can carry a first plurality of petals 172 in an oblique arrangement, and a second plurality of petals 172 in a non-oblique arrangement, in a manner analogous to that described above with respect to the flange members 162.

FIG. 3L is a representative illustration showing portions of the first tube's first and second segments 110, 115 positioned relative to a vessel entry site or point 8 by which the first segment 110 of the first tube 10 has been positioned within a vessel 2. The vessel 2 includes a superficial wall 4 and a deep vessel wall 6, in a manner readily understood by individuals having ordinary skill in the relevant art. As indicated in FIG. 3L, in various embodiments the fenestrations 140 are disposed on a flexible or semi-flexible angulatable section, element, member, or material 112 that is connected to or formed within or as a portion of the first segment 110. The first tube 10 is configured to channel a flow of blood/fluid along a least resistive pathway through the lumen with considerable laminar flow in a first direction (proximally out of the proximal exit opening 120). Once the fenestrations 140 have entered into the vessel 2, a portion of the first segment 110 distally adjacent or very near to the petals 172 can resemble a curve or an elbow by way of bending provided by the angulatable section 112. The bending causes the first tube 10 to displace or angulate. The angulatable section 112 can establish an intended or predetermined angular orientation or angle between the first portion's first and second segments 110, 115, for instance, approximately 45°. Notwithstanding, the angulatable section's range of angulation can be from 0° to 180°, or a fraction thereof. The petals 172 are disposed on the first segment 110, slightly distal to the angulatable section 112. The majority of the length of the first segment 110 extends into the vessel 2, such that the first tube's proximal exit opening 120 reside at an intended or predetermined vascular location or target site. In some embodiments, the angulatable section 112 can be structurally reinforced to enhance structural reliability, for instance, by way of one or more of material composition selection, material thickness selection, and/or the incorporation of one or more types of fibrous strands or materials (e.g., biocompatible natural or synthetic bendable fibres such as carbon fibres, optical fibres, or silk fibers), which can be oriented along predetermined directions, such as lengthwise/cross-wise/spiral-wise, relative to the elongate length of the first tube's first segment 110) in and/or through one or more portions of the angulatable section 112.

As blood/fluid is pumped into the first tube 10, a first portion of the blood/fluid exits the proximal exit opening 120 in a first set of directions D1, and a second portion of the blood/fluid exits the fenestrations 140 in a second set of directions D2, where the set of directions D2 includes directions having a vector blood/fluid flow component opposite to the set of directions D1. More particularly, the set of directions D2 includes distal vector flow components, whereas the set of directions D1 includes proximal vector flow components. Similar, analogous, or essentially identical considerations apply to embodiments in which the anchoring assembly 150 includes flange members 162.

In order to withdraw the cannula from the cannulated vessel, the user/clinician reverses the cannula insertion process by displacing or releasing the switch 170 away from the cannula's proximal end 130. The petals 172 thus retract or collapse into the wall of the first segment 110, allowing smooth withdrawal of the cannula from the vessel. Alternatively, a person having ordinary skill in the relevant art can modify the switch 170 such that advancing the switch 170 proximally towards the cannula's proximal end 130 deactivates the petals 172, while retracting the switch 170 distally away from the proximal end 130 activates the petals 172.

Representative Aspects of Blood/Fluid Indicator Assemblies

As indicated above, the cannula can include a blood/fluid indicator assembly including a blood and/or fluid indicator interface 290, a blood/fluid indicator port 190, and a fluidic passage or channel 195 therebetween. The fluid indicator interface 290, which is carried by second portion 200, is fluidically coupled to the blood/fluid indicator port 190, which is carried by or formed within an interior or inner surface of the first segment 110 of the first tube 10. The blood/fluid indicator port 190 is positioned at a predefined distance distally away from the proximal end 130, and adjacent to or near the set of fenestrations 140, but in several embodiments not proximally beyond the positions of the fenestrations 140. Different manners in which the blood/fluid indicator port 190 can be positioned on the first segment 110 are indicated in the FIGS. identified above.

Fluidic coupling of the fluid indicator interface 290 to the blood/fluid indicator port 190 can be provided by way of the channel 195, as will be readily understood by an individual having ordinary skill in the relevant art. The blood/fluid indicator port 190 and the channel 195 fluidically connected thereto are adapted to allow backward, i.e. distal, flow of blood, as well as for retrieval or withdrawal of blood samples or specimens for testing if needed. Additionally or alternatively, the channel 195 can be attached to a manometer for measurement of intra-arterial blood pressure, or to a pressure transducer device to measure vascular pressure, thereby ensuring that the cannula is inserted into the correct vessel. A person having ordinary skill in the art will readily understand that blood/fluid flowing backward along the channel 195 can be connected to any suitable blood pressure measuring apparatus for providing the clinician with knowledge of systolic and diastolic blood pressures. In various embodiments, the channel 195 is made out of any suitable transparent or translucent material, such that the presence of blood therein can be readily visually observed by the clinician. The fluid indicator interface 290 and the channel 195 can thus provide a visual indication to a clinician of the internal flow of blood/fluid within the channel 195, and also whether the anchoring elements and the fenestrations 140 have entered the cannulated vessel 2. In addition, contrast agents can be injected into the vessel through fluid indicator port 190 by way of the fluid indicator interface 290 and the channel 195, in the opposite direction to that indicated above, to perform contrast studies or angiograms of the vessel.

In some embodiments, the fluid indicator assembly can include a luminous portion, which when contacted with blood/fluid enhances the brightness thereof to create an enhanced visual indication or direct attention to fluid flow along portions of the channel 195, in a direction away from the blood/fluid indicator port 190. The luminous portion carries therein a relatively small amount of a substance that when reacted with blood/fluid causes the blood/fluid to visually appear brighter. Such a substance can include a garnet or borate single crystal containing thorium (Th) or a liquid crystal material. The luminous portion can be disposed in a variety of positions along the length of the channel 195. For example, the luminous portion can be positioned adjacent to the blood/fluid indicator port 190 so that the enhanced brightness effect provided thereby upon the blood/fluid appears visually more obvious essentially immediately after the blood/fluid has entered the blood/fluid indicator port 190. Due to differential pressure, the blood/fluid within the cannulated vessel 2 flows into the blood/fluid indicator port 190 and interacts with the luminous portion, thereby visually enhancing the brightness of the blood/fluid. The visually enhanced portion of the blood/fluid is gradually pushed along the length of the channel 195 in a distal direction towards the fluid indicator interface 290.

In several embodiments, the blood/fluid indicator port 190 once inside the cannulated vessel allows backflow of blood/fluid into and along the channel 195 to provide the clinician with a visual indication that the fenestrations 140 and the anchoring elements of the anchoring assembly 150 are in position within the vessel lumen, indicating that they clinician may safely effectuate, deploy, or activate the anchor assembly 150.

Representative Aspects of Cannula Positioning and Anchoring

Once the fenestrations 140 and the anchoring elements (e.g., flange members 162 or petals 172) of the anchoring assembly 150 have entered the vessel as indicated by one or more portions of the fluid indicator interface, the anchoring elements can be activated by the clinician, such that the anchoring elements (e.g. flange members 162 or petals 172) expand to have a cross sectional area or diameter that is larger than the entry site 8. The first tube 10 can then be partially or slightly withdrawn or displaced out of the entry site 8, causing at least some anchoring elements to contact or abut the inner surface of vessel's superficial wall 4. During this partial withdrawal of the first tube 10, such contact of one or more anchoring elements with the superficial wall 4 provides perceptible tactile feedback to a clinician performing the cannulation, such that the clinician knows that the fenestrations 140 are correctly positioned within the vessel 2. The first tube 10 can then be anchored to the patient's skin, thereby rendering the first tube 10 substantially or essentially immobile relative to the vessel 2 and fixating the cannula, in a manner readily understood by one having ordinary skill in the relevant art.

When the first tube 10 is in a correct position and anchored such as described above, an external pump, e.g. cardiopulmonary bypass machine, can transfuse or transfer blood/fluid (e.g., oxygenated blood) through the distal opening 220 at the second portion 200. The distal opening 220 is contiguous with the lumen in the cannula structure. The transfused blood/fluid from the external pump flows through the second portion 200 of the first tube 10 toward and into the first tube's first portion 100. The blood/fluid further flows into the cannulated vessel 2 and exits the first portion 100 by way of (a) the first tube's proximal exit opening 120, and (b) the fenestrations 140. That is, a first portion of the blood/fluid flowing into the first portion 100 exits the first segment 110 by way of the first tube's proximal exit opening 120, while a second portion of the blood/fluid flowing into the first portion 100 concurrently exits the first segment 110 by way of the fenestrations 140. The first portion of the blood/fluid exits and flows proximally towards the heart, while the second portion of the blood/fluid exits and flows distally to the extremities and limbs of the body. Therefore, when in use, the cannula simultaneously directs blood/fluid flow in multiple directions, including both proximal and distal directions, within the cannulated vessel 2.

An individual having ordinary skill in the relevant art will further recognize that cannula assemblies, structures, and portions thereof in accordance with embodiments of the present disclosure can exhibit dimensions which are appropriate for the type of patient or subject (e.g., an infant or child versus a full grown adult) and/or the nature of a clinical situation under consideration. Depending upon embodiment or situational details, the first tube 10 can typically (but not exclusively) have an outer diameter of Gauge 10 on the French Catheter Scale (approximately 4 millimeters which is suitable for infants), and up to Gauge 21 on the French Catheter Scale (approximately 7 millimeters which is suitable for adults). The length of the cannula may be based on cannula products produced by Edwards Lifesciences Corporation (Irvine, CA USA), Medtronic plc (Dublin, Ireland) or Maquet Holding B.V. & Co. KG (Rastatt, Germany).

Additional/Other Design Considerations

There is a tendency for a cannula to bend out of shape prior to use because of the relatively long length of the cannula. A person having ordinary skill in the relevant art will readily understand that the wavering of the cannula relates to kinking. The cannula has a thickness between the lumen of the first tube 10. There is typically at least one steel, plastic or other metal wire strengthening portion 270 suitably positioned along the thickness of the cannula. The at least one steel wire strengthening portion 270 is placed or suitably embodied by any suitable material such as plastics, clear PVC, polyurethane, polyvinyl, or any other suitable material that are commercially available. The at least one steel, plastic or other metal wire strengthening portion 270 is adapted to provide reinforcement along a portion of the first tube 10, as shown in FIG. 5.

In some embodiments, the first tube 10 includes at least one marking positioned along a surface thereof. The at least one marking is adapted to provide a visual indication of contortion of the first tube 10, i.e. whether the first tube 10 is positioned in an undesired manner or twisted relative to a cannulated vessel. Each of the at least one markings is positioned in a manner correlated with or corresponding to the positions of the fenestrations 140 to provide the clinician with a visual indication of the directions the fenestrations 140 are facing within the cannulated vessel. The at least one marking can include a first mark site and a second mark site, wherein the alignment or positioning together of both mark sites indicates that the first tube 10 is substantially straight or is formed in a straight manner. The presence of the at least one marking can mitigate the risk of accidental contortion or twisting of the first tube 10, or any part of the cannula device, while the cannula is in use or being deployed. A cannula in accordance with an embodiment of the present disclosure can thus be adapted to provide a quick indication of an angle of twist or contortion while the first tube 10 is inside of the cannulated vessel.

Figures 5, 6:
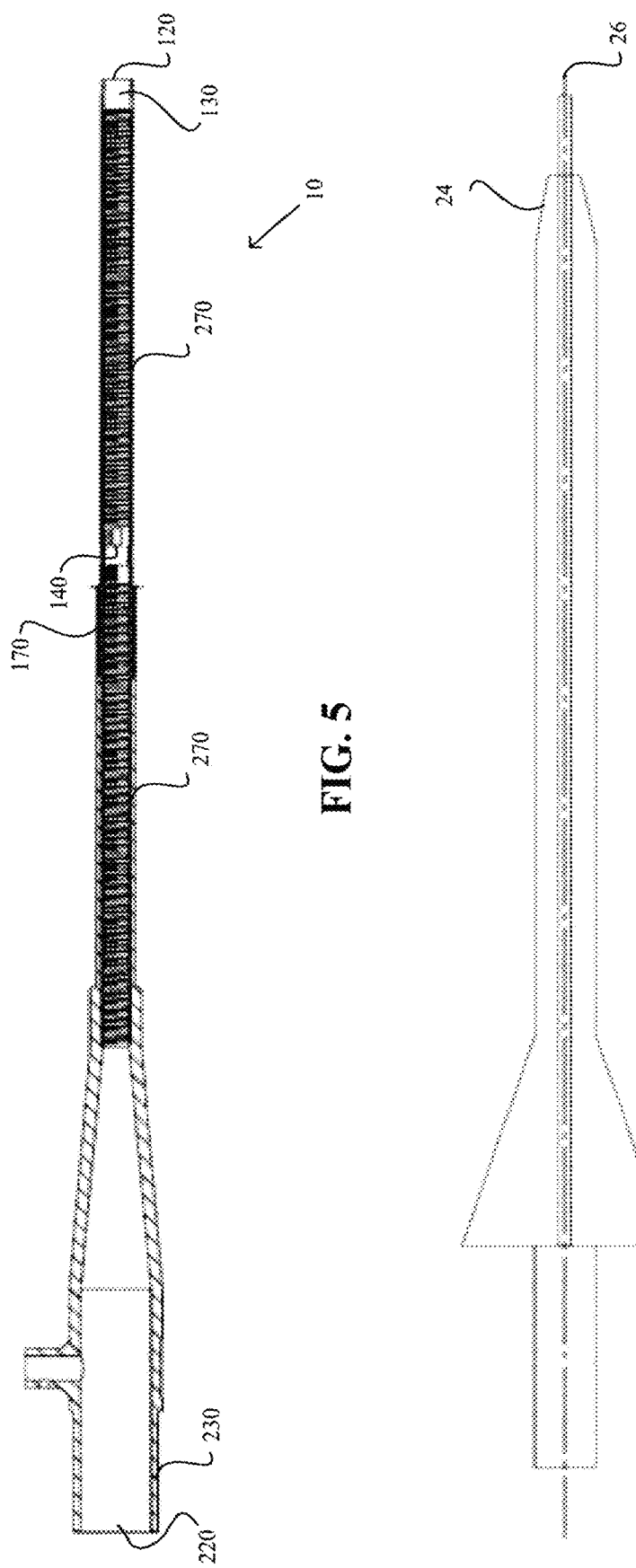
FIG. 5 is a schematic cross-sectional illustration of a cannula that carries at least one reinforcement structure, element, or material along internal portions thereof.
FIG. 6 is a schematic illustration of a dilator corresponding to a catheter in accordance with an embodiment of the present disclosure.

FIG. 6 is a schematic illustration of a second tube 20 providable or provided by or in association with a cannula assembly or structure in accordance with an embodiment of the present disclosure. One having ordinary skill in the relevant art will understand that the second tube 20 corresponds to or is a dilator assembly or dilator 20. The second tube 20 has a diameter smaller than the first tube 10, and is engageable therewith. The second tube 20 includes a central guide wire channel 22 configured for engaging with or passing a guide wire, as well as a tapered distal end 24 having a diameter that occludes the proximal exit opening 120 of the first tube 10. The tapered distal end 24 includes a through hole or opening therein 26 configured for passage of the guide wire. The guide wire can be, for instance, 0.014 inch or 0.018 inch or 0.035 inch in diameter. The guide wire has a frictional portion positioned at one end adapted to provide grip while in use. Thus, the second tube 20 facilitates or enables percutaneous insertion of the first tube 10 into the vessel 2. The second tube 20 supports, straightens, and stiffens the first tube 10, thereby smoothening entry as the first tube 10 is inserted into the vessel 2.

In a representative example femoral artery cannulation procedure for ECMO, the first tube 10 and second tube 20, henceforth simply referred to as the cannula 10 and the dilator assembly 20, are inserted into the femoral artery 2 until the blood/fluid indicator port 190 carried by the first tube's first portion 100 is inside the femoral artery 2. At this point, blood flows into the channel 195 and out through the blood/fluid indicator interface 290, thereby visually indicating to a clinician that the blood/fluid indicator port 190 is inside the femoral artery 2.

With knowledge that the cannula 10 is within the artery 2, the cannula 10 is advanced a short distance further (e.g., approximately or at least 1 centimeter), and the anchoring elements (e.g., flange members 162 or petals 172) are effectuated or activated. This further advancement of the cannula 10 into the vessel 2 ensures that the anchoring elements are well away from the superficial vessel wall 4 to avoid and prevent accidental damage to the cannulated vessel 2 while activating the anchoring elements. The cannula 10 is then gently pulled back until resistance is felt, which indicates contact of the anchoring elements (e.g., flange members 162 or petals 172) of the anchoring assembly 150 with the superficial vessel wall 4 and thus correct positioning of the cannula 10. The cannula 10 is then anchored into position to the patient's skin externally, thus providing a two-point fixation. The dilator assembly 20 is then withdrawn and the distal end 230 of the cannula 10 is attached to a pump circuit. Thus, the proximal exit opening 120 of the cannula 10 provides systemic blood flow to the body, while the fenestrations 140 provide blood flow to the extremities and limbs. The likelihood of limb ischemia is thereby greatly reduced or avoided in patients undergoing extended cardiopulmonary bypass procedures.

Aspects of particular embodiments of the present disclosure address at least one aspect, problem, limitation, and/or disadvantage associated with existing cannula designs, assemblies, or structures. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A cannula structure configured for cannulating a tubular anatomical vessel of a body of a patient, the tubular anatomical vessel having a superficial wall, the cannula structure comprising:
   a first tube insertable into the tubular anatomical vessel through a cannulation point, the first tube having each of a lumen and an elongate length, the lumen extending through the first tube, the lumen for infusing and channeling into the tubular anatomical vessel a fluid, the first tube comprising:
      a distal fluid input configured for receiving the fluid;
      a first segment having a first lumen, the first lumen extending through the first segment, the first lumen aligned with the lumen of the first tube, the first lumen fluidically coupled to the distal fluid input, wherein the first segment has a lengthwise axis that extends through the first lumen, wherein the first segment is configured for residing entirely internal to the cannulated tubular anatomical vessel, and wherein a distal portion of the first segment includes a flexible or semi-flexible angulatable section;
      a second segment having a second lumen aligned with and integrally fluidically coupled to the first lumen, wherein the second segment is distal to the first segment and the flexible or semi-flexible angulatable section, and wherein the first and second lumens form the lumen of the first tube;
      fluid outputs carried by the first segment and coupled to the distal fluid input, each fluid output configured to discharge some of the fluid received at the distal fluid input into the tubular anatomical vessel along (a) a proximal flow direction that is toward the patient's heart and parallel to the lengthwise axis of the first segment, or (b) a distal flow direction that is away from the patient's heart, parallel to the lengthwise axis of the first segment, and opposite to the proximal flow direction; and an anchoring assembly proximal to the second segment of the first tube and carried by the first segment of the first tube, wherein the anchoring assembly is configured to be inserted inside the tubular anatomical vessel during cannulation of the tubular anatomical vessel and is further configured to engage with the superficial wall of the cannulated tubular anatomical vessel adjacent or just internal to the cannulation point, wherein the anchoring assembly comprises at least one outwardly or radially displaceable structure that is coupled to an inflation tube, and which is outwardly or radially displaceable away from the first lumen beyond an exterior surface of the first segment in response to clinician application of a positive pressure that introduces air or liquid into the anchoring assembly through the inflation tube, and wherein the anchoring assembly has a distal portion disposed closest to a distal end of the cannula structure at a first circumferential position about the first segment and a proximal portion disposed closest to a proximal end of the cannula structure at a distinct second circumferential position about the first segment such that the distal portion of the anchoring assembly is closer to the second segment of the first tube than the proximal portion of the anchoring assembly, and the anchoring assembly is arranged obliquely with respect to the lengthwise axis of the first segment prior to angulation of the flexible or semi-flexible angulatable section of the first segment, wherein the flexible or semi-flexible angulatable section of the first segment is configured to displace a portion of the first segment by way of bending to establish an intended angular orientation between the first segment and the second segment once the fluid outputs carried by the first segment have entered the tubular anatomical vessel; and wherein among the fluid outputs carried by the first segment:

each fluid output that is configured to discharge some of the fluid in the proximal flow direction is disposed at a proximal end of the first segment, and each fluid output that is configured to discharge some of the fluid in the distal flow direction is disposed contiguous to the anchoring assembly.

2. The cannula structure of claim 1, wherein the anchoring assembly comprises an inflatable cuff that is disposed about the first segment, and wherein the inflation tube is fluidically coupled to a one-way valve assembly and the inflatable cuff.

3. The cannula structure of claim 1, wherein each fluid output that is configured to discharge some of the fluid in the distal flow direction is carried only on a lower half section of the first segment.

4. The cannula structure of claim 1, wherein the anchoring assembly comprises a plurality of outwardly or radially displaceable structures disposed about portions of a circumference of the first segment, and wherein the plurality of outwardly or radially displaceable structures includes a first outwardly or radially displaceable structure disposed closest to the cannula structure's distal end, and a second outwardly or radially displaceable structure distinct from the first outwardly or radially displaceable structure and disposed proximal to the first outwardly or radially displaceable structure.

5. The cannula structure of claim 4, wherein among the fluid outputs carried by the first segment that are configured to discharge some of the fluid in the distal flow direction, a first fluid output is configured to discharge a first portion of the fluid in the distal flow direction and a second fluid output is configured to discharge a second portion of the fluid in the distal flow direction, wherein the first fluid output and the second fluid output are disposed at different distal locations relative to each other along the first segment and different circumferential locations relative to each other along the first segment, and wherein the first outwardly or radially displaceable structure is disposed distal to the first fluid output, and the second outwardly or radially displaceable structure is disposed distal to the second fluid output.

6. The cannula structure of claim 1, wherein the anchoring assembly comprises (a) an inflatable cuff, or (b) a rigid or generally rigid annular fluid transport channel fluidically coupled to the at least one outwardly or radially displaceable structure.

7. The cannula structure of claim 1, further comprising a second tube configured for mating engagement with the first tube and which serves as a vessel dilator when engaged with the first tube, wherein a combined structure formed of the first tube engaged with the second tube is insertable into the tubular anatomical vessel.

8. The cannula structure of claim 1, wherein among the fluid outputs carried by the first segment, a ratio of a total cross sectional area through which fluid can be discharged in the distal flow direction to a total cross sectional area through which fluid can be discharged in the proximal flow direction is between 10 to 40%.

9. The cannula structure of claim 8, wherein each fluid output carried by the first segment that is configured to discharge some of the fluid in the distal flow direction is carried only on a lower half section of the first segment.

10. A cannula structure configured for cannulating a tubular anatomical vessel of a body of a patient, the tubular anatomical vessel having a superficial wall, the cannula structure comprising:

a first tube insertable into the tubular anatomical vessel through a cannulation point, the first tube having each of a lumen and an elongate length, the lumen extending through the first tube, the lumen for infusing and channeling into the tubular anatomical vessel a fluid, the first tube comprising:

a distal fluid input configured for receiving the fluid;

a first segment having a first lumen, the first lumen extending through the first segment, the first lumen aligned with the lumen of the first tube, the first lumen fluidically coupled to the distal fluid input, wherein the first segment has a lengthwise axis that extends through the first lumen, wherein the first segment is configured for residing entirely internal to the cannulated tubular anatomical vessel, and wherein a distal portion of the first segment includes a flexible or semi-flexible angulatable section;

a second segment having a second lumen aligned with and integrally fluidically coupled to the first lumen, wherein the second segment is distal to the first segment and the flexible or semi-flexible angulatable section, and wherein the first and second lumens form the lumen of the first tube;

a plurality of fluid outputs coupled to the distal fluid input and configured for discharging the fluid into the tubular anatomical vessel, wherein the plurality of fluid outputs comprises:

an exit opening disposed near or at a proximal end of the first segment, the exit opening configured for outputting or discharging a first portion of the fluid into the tubular anatomical vessel along a proximal flow direction that is (a) toward the patient's heart, and (b) parallel to the lengthwise axis of the first segment; and a set of fenestrations carried by distal portions of the first segment along portions of a length of the first segment and about portions of a circumference of the first segment on the flexible or semi-flexible angulatable section of the first segment, the set of fenestrations configured for outputting or discharging a second portion of the fluid into the tubular anatomical vessel such that the second portion of the fluid flows along a distal flow direction that is (a) away from the patient's heart, (b) parallel to the lengthwise axis of the first segment, and (c) opposite to the proximal flow direction; and an anchoring assembly proximal to the second segment of the first tube and carried by the first segment of the first tube near or adjacent and distal to the set of fenestrations, wherein the anchoring assembly is configured for engagement with the superficial wall of the cannulated tubular anatomical vessel adjacent or just internal to the cannulation point, wherein the anchoring assembly comprises at least one outwardly or radially displaceable structure that is coupled to an inflation tube, and which is outwardly or radially displaceable away from the first lumen beyond an exterior surface of the first segment in response to clinician application of a positive pressure that introduces air or liquid into the anchoring assembly through the inflation tube, and wherein the anchoring assembly has a distal portion disposed closest to a distal end of the cannula structure at a first circumferential position about the first segment and a proximal portion disposed closest to a proximal end of the cannula structure at a distinct second circumferential position about the first segment such that the distal portion of the anchoring assembly is closer to the second segment of the first tube than the proximal portion of the anchoring assembly, the anchoring assembly is arranged obliquely with respect to the lengthwise axis of the first segment prior to angulation of the flexible or semi-flexible angulatable section of the first segment, and each fenestration carried by the distal portions of the first segment along the portions of the length of the first segment and about the portions of the circumference of the first segment on the flexible or semi-flexible angulatable section of the first segment is disposed proximally adjacent or contiguous to the anchoring assembly after the cannula structure has been inserted into and anchored within the cannulated tubular anatomical vessel, and further wherein the anchoring assembly comprises an inflatable cuff that is disposed about the first segment, wherein the inflation tube is fluidically coupled to a one-way valve assembly and the inflatable cuff, wherein the inflatable cuff comprises an elliptical or circular ring type structure that comprises an inner layer, an outer layer, a chamber between the inner layer and the outer layer, and a plurality of flange members integrally carried by or formed from portions of the outer layer or structurally and/or fluidically coupled to or formed from portions of the outer layer.

11. A cannula structure configured for cannulating a tubular anatomical vessel of a body of a patient, the tubular anatomical vessel having a superficial wall, the cannula structure comprising:

a first tube insertable into the tubular anatomical vessel through a cannulation point, the first tube having each of a lumen and an elongate length, the lumen extending through the first tube, the lumen for infusing and channeling into the tubular anatomical vessel a fluid, the first tube comprising:

a distal fluid input configured for receiving the fluid;

a first segment having a first lumen, the first lumen extending through the first segment, the first lumen aligned with the lumen of the first tube, the first lumen fluidically coupled to the distal fluid input, wherein the first segment has a lengthwise axis that extends through the first lumen, wherein the first segment is configured for residing entirely internal to the cannulated tubular anatomical vessel, and wherein a distal portion of the first segment includes a flexible or semi-flexible angulatable section;

a second segment having a second lumen aligned with and integrally fluidically coupled to the first lumen, wherein the second segment is distal to the first segment and the flexible or semi-flexible angulatable section, and wherein the first and second lumens form the lumen of the first tube;

a plurality of fluid outputs coupled to the distal fluid input and configured for discharging the fluid into the tubular anatomical vessel, wherein the plurality of fluid outputs comprises:

an exit opening disposed near or at a proximal end of the first segment, the exit opening configured for outputting or discharging a first portion of the fluid into the tubular anatomical vessel along a proximal flow direction that is (a) toward the patient's heart, and (b) parallel to the lengthwise axis of the first segment; and a set of fenestrations carried by distal portions of the first segment along portions of a length of the first segment and about portions of a circumference of the first segment on the flexible or semi-flexible angulatable section of the first segment, the set of fenestrations configured for outputting or discharging a second portion of the fluid into the tubular anatomical vessel such that the second portion of the fluid flows along a distal flow direction that is (a) away from the patient's heart, (b) parallel to the lengthwise axis of the first segment, and (c) opposite to the proximal flow direction; and an anchoring assembly proximal to the second segment of the first tube and carried by the first segment of the first tube near or adjacent and distal to the set of fenestrations, wherein the anchoring assembly is configured for engagement with the superficial wall of the cannulated tubular anatomical vessel adjacent or just internal to the cannulation point, wherein the anchoring assembly comprises at least one outwardly or radially displaceable structure that is coupled to an inflation tube, and which is outwardly or radially displaceable away from the first lumen beyond an exterior surface of the first segment in response to clinician application of a positive pressure that introduces air or liquid into the anchoring assembly through the inflation tube, and wherein the anchoring assembly has a distal portion disposed closest to a distal end of the cannula structure at a first circumferential position about the first segment and a proximal portion disposed closest to a proximal end of the cannula structure at a distinct second circumferential position about the first segment such that the distal portion of the anchoring assembly is closer to the second segment of the first tube than the proximal portion of the anchoring assembly, the anchoring assembly is arranged obliquely with respect to the lengthwise axis of the first segment prior to angulation of the flexible or semi-flexible angulatable section of the first segment, and each fenestration carried by the distal portions of the first segment along the portions of the length of the first segment and about the portions of the circumference of the first segment on the flexible or semi-flexible angulatable section of the first segment is disposed proximally adjacent or contiguous to the anchoring assembly after the cannula structure has been inserted into and anchored within the cannulated tubular anatomical vessel, and further wherein the anchoring assembly comprises an inflatable cuff that comprises an elliptical or circular ring type structure, wherein the at least one outwardly or radially displaceable structure is formed as an outer layer of the inflatable cuff and a plurality of flange members carried by the outer layer and which are configured to protrude away from the first lumen in response to inflation of the inflatable cuff.

12. The cannula structure of claim 11, wherein each of the plurality of flange members protrudes away from and beyond the exterior surface of the first segment responsive to inflation of the inflatable cuff while the inflatable cuff (i) resides at least partially within a thickness of a wall of the first segment, or (ii) remains internal to the exterior surface of the first segment.

* * * * *